United States Patent [19]
Fukuda et al.

[11] Patent Number: 6,136,580
[45] Date of Patent: Oct. 24, 2000

[54] β-1-6-N-ACETYLGLUCOSAMINYLTRANSFERASE THAT FORMS CORE 2, CORE 4 AND I BRANCHES

[75] Inventors: Minoru Fukuda, San Diego; Jiunn-Chern Yeh, La Jolla, both of Calif.

[73] Assignee: The Burnham Institute, La Jolla, Calif.

[21] Appl. No.: 09/233,506

[22] Filed: Jan. 19, 1999

[51] Int. Cl.$^7$ .............................. C12N 9/10; C12P 19/18; A61K 16/00
[52] U.S. Cl. ............................... 435/193; 435/6; 435/7.4; 435/97; 530/380; 530/350; 530/326; 530/327; 536/23.2
[58] Field of Search ................................. 435/193, 97, 6, 435/7.4; 530/350, 326, 327; 536/23.2

[56] References Cited

U.S. PATENT DOCUMENTS 5,360,733  11/1994  Fukuda et al. ........................... 435/193
5,484,590   1/1996  Fukuda et al. ........................... 424/94.5

OTHER PUBLICATIONS

Bierhuizen et al., "Expression of the developmental I antigen by a cloned human cDNA encoding a member of a β–1,6–N–acetylglucosaminyltransferase gene family", *Genes & Development*, 7:468–478 (1993).

Bierhuizen and Fukuda, "Expression cloning of a cDNA encoding UDP–GlcNac:Galβ1–3–GalNAc–R (GlcNAc to GalNAc) β1–6GlcNAc transferase by gene transfer into CHO cells expressing polyoma large tumor antigen", *Proc. Natl. Acad. Sci. USA*, 89:9326–9330 (1992).

Bierhuizen et al., "Expression of a differentiation antigen and Poly–N–acetyllactosaminyl O–Glycans directed by a cloned core 2 β–1,6–N–acetylglucosaminyltransferase", *J. Biol. Chem.*, 269:4473–4479.

Brockhausen et al., "Mucin synthesis: Conversion of $R_1β1–3Gal–R_2$ to $R_1–β1–3(GlcNAcβ1)Gal–R_2$ and of $R_1β1–3GalNAc–R_2$ to $R_1β1–3(Glc$ *Eur. J. Biochem.*, 157:463–474 (1986).

Edge et al., "Structure of the O–Linked Oligosaccharides from a Major Thyroid Cell Surface Glycoprotein", *Arch. Biochem. Biophys.*, 343:73–80 (1997).

Ellies et al., "Core 2 oligosaccharide biosynthesis distinguishes between selectin ligans essential for leukocyte homing and inflammation", *Immunity*, 9(6):881–890 (1998).

Gu et al., "Biosynthesis of blood group I and I antigens in rat tissues", *J. Biol. Chem.*, 267:2994–2999 (1992).

Matilla et al., "The centrally acting β1,6N–acetylglucosaminyltranferase (GlcNAc to Gal)", *J. Biol. Chem.*, 273:27633–27639 (1998).

Nakayama et al., "A human polysialytransferase directs in vitro synthesis of polysialic acid", *J. Biol. Chem.*, 271:1829–1832 (1996).

Paulson et al., "Glcosyltransferases: Structure, localization, and control of cell type–specific glycosylation", *J. Biol. Chem.*, 264:17615–17618 (1989).

Piller et al., "Biosynthesis of blood group I antigens", *J. Biol. Chem.*, 259:13385–13390 (1998).

Ropp et al., "Mucin biosynthesis: Purification and characterization of a mucin β6N–acetylglucosaminyltranferase", *J. Biol. Chem.*, 266:23863–23871 (1991).

Sasaki et al., "Carbohydrate structure of erythropoietin expressed in Chinese hamster ovary cells by a human erythropoietin cDNA", *J. Biol. Chem.*, 262:12059–12076 (1987).

Smith et al., "Transfer and expression of a murine UDP–Gal:beta–D–Gal–alpha 1,3–galactosyltranferase gene in transfected Chinese hamster ovary cells: Competition reactions between the alpha 1,3–galactosyltransferase and the endogenous alpha 2,3–sialyltransferase", *J. Biol. Chem.*, 265:6225–6234 (1990).

Ujita et al., "Synthesis of poly–N–acetyllactosamine in core 2 branched O–glycans", *J. Biol. Chem.*, 273:34843–34849 (1998).

Varki, "Perspectives Series: Cell adhesion in vascular biology", *J. Clin. Invest.*, 99:158–162 (1997).

Vavasseur et al., "Synthesis of O–glycan core 3: Characterization of UDP–GlcNAc: GalNAc–R β3–N–acetyl–glucosaminyltransferasea activity from colonic mucosal tissues and lack of the activity in human cancer cell lines", *Glycobiology*, 5:351–357 (1995).

Yang et al., "Alterations of O–glycan biosynthesis in human colon cancer tissues", *Glycobiology*, 4:873–884 (1994).

Adams et al., GenBank Accession No: AA307800, Apr. 18, 1997.

*Primary Examiner*—Rebecca E. Prouty
*Assistant Examiner*—Richard Hutson
*Attorney, Agent, or Firm*—Campbell & Flores LLP

[57] ABSTRACT

The present invention provides a substantially pure C2GnT-M polypeptide or a functional fragment or derivative thereof, wherein C2GnT-M is characterized as a polypeptide having core 2, core 4 and I branching β-1→6-N-acetylglucosaminyltransferase activities. The invention also provides a substantially pure C2GnT-M peptide, wherein the peptide is immunogenic. Also provided is a method of modifying an acceptor molecule by contacting the acceptor molecule with a substantially pure C2GnT-M polypeptide or a functional fragment under conditions that allow addition of core 2, core 4 or I GlcNAc linkages to the acceptor molecule, and an acceptor molecule produced by the method. Also provided is a substantially pure nucleic acid molecule having substantially the nucleic acid sequence designated SEQ ID NO: 1, or the complement thereof. The invention also provides a substantially pure nucleic acid molecule encoding C2GnT-M or a functional fragment or derivative thereof, or the complement of the nucleic acid molecule, wherein C2GnT-M is characterized as a polypeptide having core 2, core 4 and I branching P-1→6-N-acetylglucosaminyltransferase activities. Also provided are vectors and host cells containing nucleic acid molecules encoding C2GnT-M or a functional fragment or derivative thereof. A substantially pure oligonucleotide having a nucleotide sequence corresponding to or complementary to at least 15 nucleotides from SEQ ID NO: 1, SEQ ID NO: 9 or SEQ ID NO: 13 is also provided. The invention further provides an antibody or antigen binding fragment thereof that is specifically reactive with C2GnT-M or with a functional fragment or derivative hereof. Methods of detecting the presence of C2GnT-M in sample are also provided.

17 Claims, 10 Drawing Sheets

```
   1'                                                   ATACAGGTCC
                                                        ****** ***
 308 ACCTCTCCCTCACCAGAGACTGTGAGCACTTCAAGGCTGAAAGGAAGTTCATACAGTTCC

11' CACTGAGCAAGGAAGAGGCCAGCTTCCCCATTGCGTACTCCATGGTGGTGCATGAGAAGA
      **********  *******    *****  *****  *****  ****** * **********
 368 CACTGAGCAAAGAAGAGGTGGAGTTCCCTATTGCATACTCTATGGTGATTCATGAGAAGA

71' TTGAGAACTTCGAAAGGTTGCTGCGAGCTGTGTACACCCCTCAGAATGTATACTGTGTCC
      ****  *****  ****** *  ************** **********  ************
 428 TTGAAAACTTTGAAGGCTACTGCGAGCTGTGTATGCCCCTCAGAACATATACTGTGTCC

131' ACATGGATCAGAAGTCTTCAGAACCCTTTAAGCAGGCAGTCGGGGCCATCGTGTCATGCT
      * ***** *******  ***** * ** **  **** ***    ** ** * ** ****
 488 ATGTGGATGAGAAGTCCCCAGAAACTTTCAAAGAGGCGGTCAAAGCAATTATTTCTTGCT

191' TC
      **
 548 TCCCAAATGTCTTCATAGCCAGTAAGCTGGTTCGGGTGGTTTATGCCTCCTGGTCCAGGG
```

Figure 9A

```
  1'                                                              I
                                                                  *
 61" KLPAKRSINCSGVTRGDQEAVLQAILNNLEVKKKREPFTDTHYLSLTRDCEHFKAERKFI

2' QVPLSKEEASFPIAYSMVVHEKIENFERLLRAVYTPQNVYCVHMDQKSSEPFKQAVGAIV
     * ******..********.*****************.***.****.*.**.*.**.** **.
121" QFPLSKEEVEFPIAYSMVIHEKIENFERLLRAVYAPQNIYCVHVDEKSPETFKEAVKAII

62' SCF
     ***
181" SCFPNVFIASKLVRVVYASWSRVQADLNCMEDLLQSSVPWKYFLNTCGTDFPIKSNAEMV
```

Figure 9B

```
  1'      CTATTGAAAGGGCAGAACAGTATGGAGTCAGAGGTACCACCTCCACATAAAAAAT
          * ***** ***   *** ** ****************** ***   ** *** **
728"      TCAAGATGTTGAATGGGAGGAATAGCATGGAGTCAGAGGTACCTCCTAAGCACAAAGAAA

56'      CCCGCTGGAAATATCACTATGAGG---TGACAGACACATTGCACATGACCAGCAAGAGGA
          ******************* *****    *** ********* *** * **** ***** **
788"      CCCGCTGGAAATATCACTTTGAGGTAGTGAGAGACACATTACACCTAACCAACAAGAAGA

113'      AGACGCCGCCACCTAATAACCTAACCATGTTCACT
          **    ** ** *** ****    **** ***** **
848"      AGGATCCTCCCCCTTATAATTTAACTATGTTTACAGGGAATGCGTACATTGTGGCTTCCC
```

Figure 10A

```
  1'      LLKGQNSMESEVPPPHKKSEWKYHYEVT-DTLHMTSKRKTPPPNNLTMFTCN
          .*.*.********  **..*****.**.  ****.*.*.*.*** ******
241"      QALKMLNGRNSMESEVPPKHKETRWKYHFEVVRDTLHLTNKKKDPPPYNLTMFTGNAYIV
```

Figure 10B

β-1-6-N-ACETYLGLUCOSAMINYLTRANSFERASE THAT FORMS CORE 2, CORE 4 AND I BRANCHES

This invention was made in part with Government support under Grant Nos. CA33000 and CA71932. The Government may have certain rights in this invention.

BACKGROUND OF THE INVENTION

1. Field of the Invention

This invention relates generally to the fields of biochemistry and cell biology and, more specifically, to a novel β-1→6-N-acetylglucosaminyltransferase.

2. Background Information

The carbohydrate components of cell surface glycoproteins play important roles in a variety of biological processes, such as cell-cell interaction, cell adhesion, proliferation and differentiation. Specific sets of carbohydrates are characteristic for different stages of differentiation, and often these carbohydrates are recognized by specific antibodies, thus providing differentiation antigens. The aberrant expression of cell surface glycoproteins has been associated with various pathologies, including immunodeficiency syndromes and cancer.

Sialylated fucosylated lactosamines are a specific class of carbohydrates whose expression on the cell surface is regulated during normal development and pathogenesis. These sialylated fucosylated lactosamines are critical components of ligands of a family of cell adhesion receptors called selectins, which include E-, P- and L-selectins. Selectins normally play a role in mediating cell adhesion between leukocytes and the vascular endothelial surface, and therefore are critical in normal immune surveillance as well as in leukocyte recruitment to sites of acute and chronic inflammation. During metastasis of tumor cells, interactions between sialyl Le$^x$-containing ligands and selectins appear to be important in modulating the adhesion of carcinoma cells to endothelial cells in target organs. For example, increased expression of sialyl Le$^x$ and sialyl Le$^a$ on the surface of carcinoma cells is positively associated with metastatic potential.

Sialyl Le$^x$ and sialyl Le$^a$ determinants are present in a variety of mucin-type glycoproteins that contain (O)-linked oligosaccharides, or O-glycans. Sialyl Le$^x$, which has the structure NeuNAcα2→3Galβ1→4(Fucα1→3)GlcNacβ→R, and sialyl Le$^a$, which has the structure NeuNAcα2→3Galβ1→3(Fucα1→4)GlcNacβ→R, are formed by modifications to oligosaccharides having the branched core 2 structure Galβ1→3(GlcNAcβ1→6)GalNAc, as shown in FIG. 2, and also by modifications to oligosaccharides with linear or branched poly-N-acetyllactosamine repeats (Galβ1→4GlcNacβ1→3), such as i or I antigen core structures.

As shown in FIG. 1, core 2 oligosaccharides are derived from core 1 structures by the action of a core 2 β-1→6-N-acetylglucosaminyltransferase (C2GnT). A human enzyme with core 2 β1→6 N-acetylglucosaminyltransferase activity, now designated C2GnT-L, has been purified and cloned and is the subject of U.S. Pat. No. 5,360,733. Recently, increased expression of C2GnT-L has been shown to be closely correlated with invasiveness of colorectal cancer cells, and ectopic expression of this enzyme in T cells is associated with an impaired immune response.

FIG. 3 shows the biosynthesis of the I branched antigen structure. The conversion of a linear poly-N-acetyllactosamine designated "i antigen" to the branched poly-N-acetyllactosamine designated "I antigen" is due to activity of an I-branching β1→6 N-acetylglucosaminyltransferase (IGnT). A human I-branching β1→6 N-acetylglucosaminyltransferase is the subject of U.S. Pat. No. 5,484,590. I branched poly-N-acetyllactosamines expressing blood group H antigens have much better avidity to anti-ABO antibodies than linear i poly-N-acetyllactosamines, and are implicated in detrimental immune responses when mother and fetus have incompatible blood group antigens. Additionally, more highly branched sialyl Le$^x$-containing oligosaccharides have greatly increased affinity for selecting. Therefore, highly branched sialyl Le$^x$-containing oligosaccharides could be administered as therapeutic agents that act as selectin ligand agonists or antagonists.

Core 4 oligosaccharides are derived from core 3 structures by the action of a core 4 β-1→6-N-acetylglucosaminyltransferase (C4GnT), as shown in FIG. 1. Like core 2 and I-branched oligosaccharides, core 4-containing oligosaccharides are also important in normal development and in pathological conditions. For example, core 4 containing oligosaccharides are normally found in cells of the gastrointestinal tract. The levels of core 4 structures have been observed to be reduced in colon carcinoma cells.

These observations establish core 2, core 4 or I branching β1→6 N-acetylglucosaminyltransferases and heir products as important mediators of normal development and differentiation, and additionally implicate these molecules in pathological conditions such as inflammation, tissue rejection and tumor metastasis. Identifying glycosyltransferases and their products is a critical step in preparing reagents that can be used to diagnose, prevent or treat these pathologies. Thus, a need exists to identify and characterize members of the glycosyltransferase enzyme family. The present invention satisfies this need and provides related advantages as well.

SUMMARY OF THE INVENTION

The present invention provides a substantially pure C2GnT-M polypeptide or a functional fragment or derivative thereof, wherein C2GnT-M is characterized as a polypeptide having core 2, core 4 and I branching β-1-6-N-acetylglucosaminyltransferase activities. The invention also provides a substantially pure C2GnT-M peptide, wherein the peptide is immunogenic. Also provided is a method of modifying an acceptor molecule by contacting the acceptor molecule with a substantially pure C2GnT-M polypeptide or a functional fragment under conditions that allow addition of core 2, core 4 or I GlcNAc linkages to the acceptor molecule, and an acceptor molecule produced by the method.

Also provided is a substantially pure nucleic acid molecule having substantially the nucleic acid sequence designated SEQ ID NO: 1, or the complement thereof. The invention also provides a substantially pure nucleic acid molecule encoding C2GnT-M or a functional fragment or derivative thereof, or the complement of the nucleic acid molecule, wherein C2GnT-M is characterized as a polypeptide having core 2, core 4 and I branching β-1–6-N-acetylglucosaminyltransferase activities. Also provided are vectors and host cells containing nucleic acid molecules encoding C2GnT-M or a functional fragment or derivative thereof. A substantially pure oligonucleotide having a nucleotide sequence corresponding to or complementary to at least 15 nucleotides from SEQ ID NO: 1, SEQ ID NO: 9 or SEQ ID NO: 13 is also provided.

The invention further provides an antibody or antigen binding fragment thereof that is specifically reactive with C2GnT-M or with a functional fragment or derivative thereof. Methods of detecting the presence of C2GnT-M in a sample are also provided.

BRIEF DESCRIPTION OF THE FIGURES

FIG. 4 shows the nucleotide sequence (SEQ ID NO: 1) and deduced amino acid sequence (SEQ ID NO: 2) of human C2GnT-M.

FIG. 5 shows the homology between human C2GnT-M (SEQ ID NO: 2), C2GnT-L (SEQ ID NO: 3) and IGnT (SEQ ID NO: 4) amino acid sequences.

FIG. 9A shows the nucleotide sequence (SEQ ID NO: 9) of the mouse C2GnT-M CCL1 fragment (top sequence) aligned with the human C2GnT-M nucleotide sequence (fragment of SEQ ID NO: 1). FIG. 9B shows the amino acid sequence (SEQ ID NO: 10) encoded by the mouse C2GnT-M CCL1 fragment (top sequence) aligned with the human C2GnT-M amino acid sequence (fragment of SEQ ID NO: 2).

FIG. 10A shows the nucleotide sequence (SEQ ID NO: 13) of the mouse C2GnT-M IS3 fragment (top sequence) aligned with the human C2GnT-M nucleotide sequence (fragment of SEQ ID NO: 1). FIG. 10B shows the amino acid sequence (SEQ ID NO: 14) encoded by the mouse C2GnT-M IS3 fragment (top sequence) aligned with the human C2GnT-M amino acid sequence (fragment of SEQ ID NO: 2).

Definitions

Figure 1:
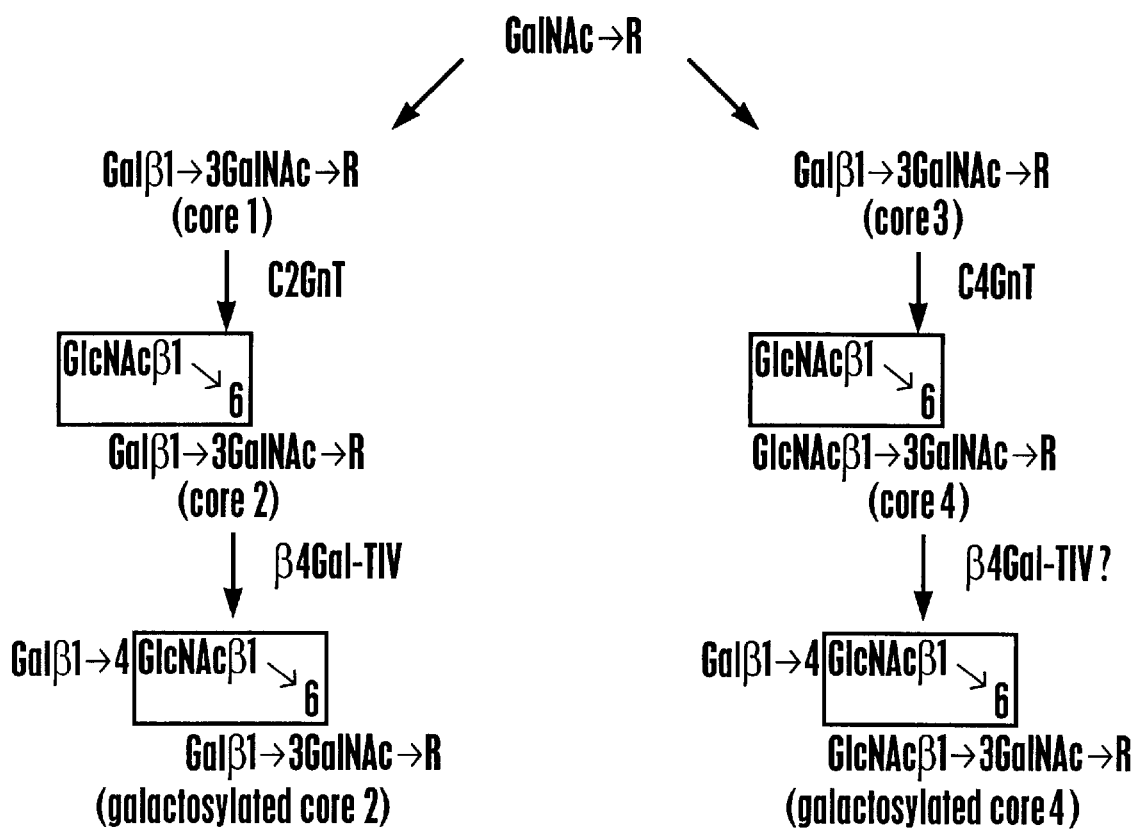
FIG. 1 shows the structure and biosynthesis of O-glycans.
Figure 2:
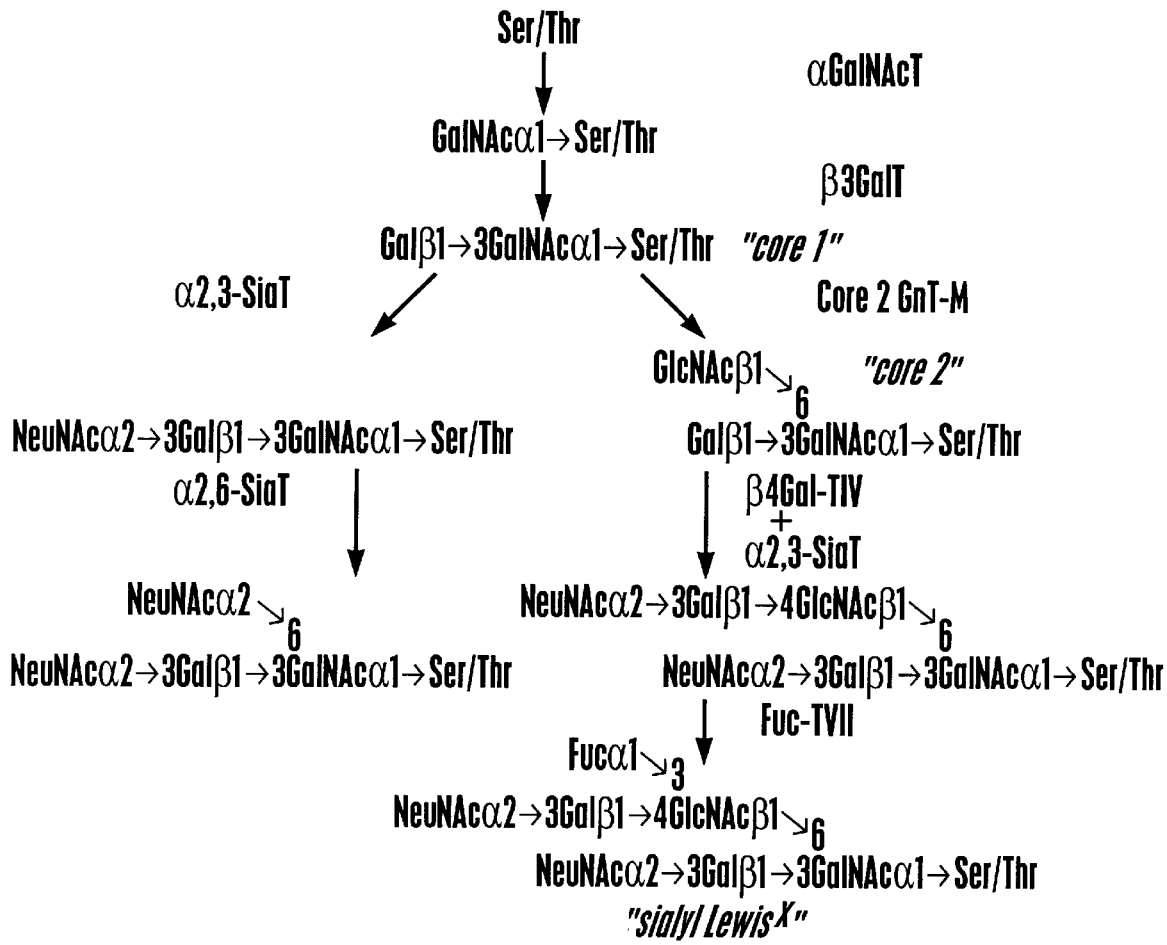
FIG. 2 shows the structure and biosynthesis of sialyl Lewis$^x$ in core 2 branched O-glycans.
Figure 3:
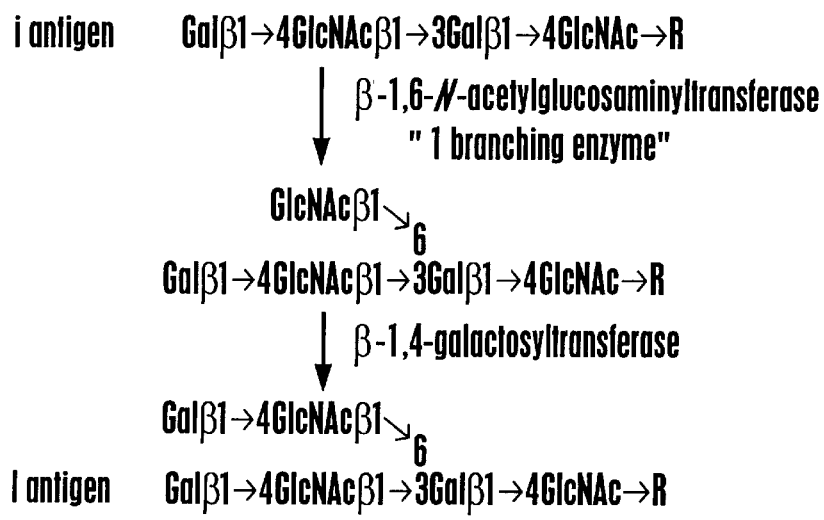
FIG. 3 shows the structure and biosynthesis of i and I antigens.

The term "C2GnT-M," as used herein, refers to a mammalian polypeptide characterized as having core 2, core 4 and I branching β-1–6-N-acetylglucosaminyltransferase activities. The term includes polypeptides that correspond, for example, to human, mouse, rat, porcine, bovine and ovine C2GnT-M. Preferably, C2GnT-M will be a human or mouse C2GnT-M, more preferably a human C2GnT-M.

The term "functional fragment," as used herein with regard to a polypeptide, refers to portions of that polypeptide that are capable of exhibiting or carrying out a biological activity exhibited by the polypeptide as a whole. With respect to a C2GnT-M polypeptide, a functional fragment can have core 2, core 4 or I branching β-1–6-N-acetylglucosaminyltransferase activities, UDP-GlcNAc binding activity, or any combination of these activities. A functional fragment of C2GnT-M usually includes at least 5 contiguous amino acid residues from C2GnT-M, preferably at least 20 amino acids, more preferably at least 50 amino acids, and often at least 100 amino acids.

The term "core 2," as used herein, is intended to mean the core structure Galβ1→3(GlcNAcβ1→6)GalNAcα1→R. "Gal" refers to galactose. "GalNAc" refers to N-acetylgalactosamine. "GlcNAc" refers to N-acetylglucosamine. "R" can be a serine or threonine residue of a peptide or protein or, for example, an octyl, O-methyl, p-nitrophenol, aminopyridine, or other convenient moiety.

The term "core 2 β-1→6-N-acetylglucosaminyltransferase activity," as used herein, is intended to mean catalysis of the β1→6 linkage of a GlcNAc moiety to an acceptor molecule containing the core 1 structure Galβ1→3GalNAc→R, to form a core 2 structure.

The term "core 4," as used herein, is intended to mean the core structure GlcNacβ1→3 (GlcNAcβ1→6) GalNAcα1→R.

The term "core 4 β1→6 N-acetylglucosaminyltransferase activity," as used herein, is intended to mean catalysis of the β1→6 linkage of a GlcNAc moiety to an acceptor molecule containing the core 3 structure GlcNAcβ1→3GalNAcα1→R, to form a core 4 structure.

The term "I branching β1→6 N-acetylglucosaminyltransferase activity," as used herein, is intended to mean catalysis of the β1→6 linkage of a GlcNAc moiety to an acceptor molecule containing the "i antigen" core structure, Galβ1→4GlcNacβ1→3Galβ1→4GlcNac→R, to form Galβ1→4GlcNacβ1→3(GlcNAcβ1→6)Galβ1→4GlcNac→R.

The term "substantially pure," as used herein in regard to nucleic acids and polypeptides of the invention is intended to mean that the molecule is removed, isolated or separated from its natural environment. A "substantially pure" molecule of the invention is at least 60% free, preferably 75% free, more preferably 90% free from other components with which it is naturally associated.

The term "nucleic acid molecule" as used herein refers to an oligonucleotide or polynucleotide of natural or synthetic origin. A nucleic acid molecule can be single- or double-stranded genomic DNA, cDNA or RNA, and represent either the sense or antisense strand or both. For example, a nucleic acid molecule indicated to encode a particular polypeptide can be either the sense or antisense nucleic acid molecule, or both.

The term "operatively linked," as used herein, is intended to mean that the nucleic acid molecule is positioned with respect to a promoter in such a manner that the promoter will direct the transcription of RNA using the nucleic acid molecule as a template.

The term "corresponding to," as used herein in regard to a nucleic acid sequence, includes the described sequence and sequences having one or more additions, deletions or substitutions that do not substantially reduce the ability of the molecule to hybridize under stringent conditions to the recited sequence. For example, a nucleic acid sequence that corresponds to a C2GnT-M nucleic acid sequence can have greater than about 70% homology with a C2GnT-M sequence, preferably greater than about 80% homology, more preferably greater than about 90% homology with a native C2GnT-M sequence. Similarly, the term "complementary to," or "complement thereof," as used herein, is intended to mean an nucleic acid sequence that corresponds to the antisense strand of the recited sequence.

The term "derivative" of a C2GnT-M polypeptide or fragment thereof, as used herein, refers to an amino acid sequence that contains minor modifications to the native amino acid sequence. Such modifications can be made, for example, to optimize the stability, bioactivity or bioavailability of the polypeptide, or to facilitate its expression or purification. The alterations contemplated in a derivative of the invention include additions, deletions, or substitutions of one or more amino acids with respect to the native sequence.

A derivative can have "conservative" changes, wherein a substituted amino acid has similar structural or chemical properties, e.g., substitution of an apolar amino acid with another apolar amino acid (such as replacement of leucine with isoleucine). The derivative can also have "nonconservative" changes, wherein a substituted amino acid has different but sufficiently similar structural or chemical properties that permits such a substitution without adversely affecting the desired biological activity, e.g., replacement of an amino acid with an uncharged polar R group with an amino acid with an apolar R group (such as replacement of glycine with tryptophan), replacement of an amino acid with a charged R group with an amino acid with an uncharged Polar R group (such as replacement of lysine with asparagine), or replacement of a phosphorylated residue with an acidic residue (such as replacement of a phosphorylated serine, threonine or tyrosine with a glutamic acid or aspartic acid).

| Amino Acid | Radical | 3-Letter | 1-Letter |
|---|---|---|---|
| Amino Acids - Apolar R Groups | | | |
| alanine | methyl | ala | A |
| valine | 2-propyl | val | V |
| leucine | 2-methylpropyl | leu | L |
| isoleucine | 2-butyl | ile | I |
| proline | propyl* - cyclized | pro | P |
| phenylalanine | benzyl | phe | F |
| trytophan | 3-indolylmethl | tyr | W |
| methionine | methylthioethyl | met | M |
| Amino Acids - Uncharged Polar R Groups | | | |
| glycine | H | gly | G |
| serine | hydroxymethyl | ser | S |
| threonine | 1-hydroxyethyl | thr | T |
| cysteine | thiolmethyl | cys | C |
| tyrosine | 4-hydroxyphenylmethyl | tyr | Y |
| asparagine | aminocarbonylmethyl | asn | N |
| glutamine | aminocarbonylethyl | gln | Q |
| Amino Acids - Charged R Groups | | | |
| aspartic acid | carboxymethyl | asp | D |
| glutamic acid | carboxyethyl | glu | E |
| lysine | 4-aminobutyl | lys | K |
| arginine | 3-guanylpropyl | arg | R |
| histidine | 4-imidazoylmethyl | his | H |

Guidance in determining which amino acid residues may be modified as indicated above without abolishing the desired biological functionality may be determined using computer programs well known in the art, for example, DNASTAR software.

In addition, a derivative may also result from chemical or enzymatic modifications to the encoded polypeptide, including but not limited to the following, replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation. Further, a derivative may also result from the substitution of an L-configuration amino acid with its corresponding D-configuration counterpart.

The term "acceptor molecule," as used herein, refers to a molecule that is acted upon, or "modified," by a protein having enzymatic activity. For example, an acceptor molecule can be a molecule that accepts the transfer of a GlcNAc monosaccharide due to a core 2, core 4 or I-branching glycosyltransferase activity of a C2GnT-M polypeptide of the invention. An acceptor molecule may be in either a substantially pure form or present in an impure form such as, for example, in a host cell of the invention. An acceptor molecule may be a natural molecule, such as, for example, a polypeptide, or be completely or partially synthesized. An acceptor molecule, if desired, can already contain one or more sugar residues, or be further modified to contain additional sugar residues.

The term "pharmaceutically acceptable carrier," as used herein, is any compound that is appropriate for administration to an individual and which acts to maintain or enhance the stability or bioavailability of a therapeutic agent of the invention. Pharmaceutically acceptable carriers are well known in the art and include aqueous solutions such as water and physiologically buffered saline, oils and emulsions. Other pharmaceutically acceptable carriers that can act as stabilizers or excipients include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; and lipids or liposomes. A therapeutic agent can also be formulated with a carrier such as a biodegradable polymer or a micropump that provides for controlled slow release of the agent.

The term "effective amount," as used herein, refers to a dosage of a therapeutic agent of the invention that is sufficient to prevent, treat or reduce the severity of a pathology mediated by aberrant expression of C2GnT-M or mediated by molecules with core 2, core 4 or I branched oligosaccharides. Appropriate formulations, dosages and routes of delivery for administering an effective amount of a therapeutic agent of the invention are well known to those skilled in the art and can be determined for human patients, for example, from animal models. The dosage required to be therapeutically effective can depend, for example, on such factors as the severity of the pathology, the route and form of administration, the bio-active half-life of the molecule being administered, the weight and condition of the individual, and previous or concurrent therapies, and can be determined by those skilled in the art. One skilled in the art will recognize that the condition of the patient needs to be monitored throughout the course of therapy and that the amount of the composition that is administered can be adjusted accordingly.

The term "specifically reactive," as used herein in relation to an antibody, is intended to mean high affinity binding to C2GnT-M in a binding assay, such as an immunoblot or ELISA assay, without substantial cross-reactivity with other polypeptides such as C2GnT-L or IGnT. A specifically reactive antibody can have an affinity constant of greater than $10^5$ $M^{-1}$, preferably greater than $10^7$ $M^{-1}$, more preferably greater than $10^9$ $M^{-1}$, for C2GnT-M or a characteristic fragment therefrom.

The term "detectable moiety," as used herein, refers to moieties that can be stably attached in any manner to a molecule, such as a nucleic acid or antibody, so as to render the molecule detectable by analytical methods. Specific examples of detectable moieties that can be detected by analytical means include enzymes, radioisotopes, fluorochromes, chemiluminescent markers, and biotin.

The term "sample," as used herein, is intended to mean any biological fluid, cell, tissue, organ or portion thereof, that includes or potentially includes cells expressing C2GnT-M, and includes samples present in an individual as well as samples obtained or derived from the individual. For example, a sample can be a histologic section of a specimen obtained by biopsy, or cells that are placed in or adapted to tissue culture. A sample further can be a subcellular fraction or extract, such as a membrane fraction. A sample can be prepared by methods known in the art suitable for the particular format of the detection method.

DETAILED DESCRIPTION OF THE INVENTION

The present invention relates to a novel, multi-functional β-1→6-N-acetylglucosaminyltransferase with core 2, core 4 and I branching activities, designated C2GnT-M. In particular, the invention provides substantially pure C2GnT-M polypeptides and nucleic acids, antibodies specifically reactive with C2GnT-M, and methods involving such compositions.

In contrast to previously characterized β-1→6-N-acetylglucosaminyltransferases with single activities, C2GnT-M described herein has core 2, core 4 and I branching activities in a single enzyme. Therefore, C2GnT-M can be advantageously used to prepare molecules that have core 2, core 4 and I branches in a single, efficient reaction, thus reducing the labor and cost involved in preparing such oligosaccharides. The extent of branching of sialyl Le$^x$-containing oligosaccharides and the number of carbohydrate substituents displayed on a polypeptide backbone affect the avidity, affinity and selectively of the ligand for particular selectins. Therefore, C2GnT-M can be advantageously used to prepare molecules having highly branched sialyl Lex structures, which can serve as high affinity ligands for E-, P- and L-selectins. Such selectin ligands can be used therapeutically to modulate immune reactions, such as inflammation and tissue rejection, as well as to prevent or inhibit tumor metastasis.

The invention provides a substantially pure C2GnT-M polypeptide or a functional fragment or derivative thereof, wherein C2GnT-M is characterized as a polypeptide having core 2, core 4 and I branching β-1→6-N-acetylglucosaminyltransferase activities. Human C2GnT-M can be further characterized as a polypeptide of 438 amino acid residues having a predicted molecular weight of 50,963 Da and a predicted type II membrane topology. An exemplary C2GnT-M of the invention has substantially the amino acid sequence shown in FIG. 4 (SEQ ID NO: 2). Another exemplary C2GnT-M of the invention contains substantially the amino acid sequence shown in FIG. 9B (SEQ ID NO: 10) and FIG. 10B (SEQ ID NO: 14).

As disclosed herein, C2GnT-M is a membrane protein that is predominantly expressed in colon, small intestine, trachea, stomach and thyroid, as well as in cancer cells such as the A549 lung carcinoma cell line. Therefore, C2GnT-M or a functional fragment thereof can be purified from such tissues or cells by biochemical procedures routinely used in the art, including membrane fractionation, chromatography, electrophoresis and affinity methods. For example, cell membrane fractions can be isolated, detergent solubilized, applied to a UDP-hexanolamine affinity column, and the substantially pure C2GnT-M polypeptide eluted with UDP-GlcNAc. Additionally, C2GnT-M can be substantially purified by immunoaffinity methods known in the art, using the C2GnT-M antibodies described herein. Substantially pure C2GnT-M and its functional fragments and derivatives can also be prepared from nucleic acids encoding C2GnT-M, using recombinant procedures known in the art and described herein.

The invention also provides functional fragments and derivatives of C2GnT-M that have one or more of the biological activities of full-length C2GnT-M. A biological activity of a C2GnT-M fragment can be, for example, one or any combination of the core 2 β-1→6-N-acetylglucosaminyltransferase, core 4 β-1→6-N-acetylglucosaminyltransferase or I-branching β-1→6-N-acetylglucosaminyltransferase activities of C2GnT-M. Additionally or alternatively, a biological activity of a C2GnT-M fragment can be UDP-GlcNAc binding activity.

A functional fragment of C2GnT-M can include, for example, one or more of the regions of the C2GnT-M catalytic domain having high homology to C2GnT-L and IGnT, designated A, B and C regions, as shown in FIG. 5. A specific example of a functional fragment of C2GnT-M is a catalytic domain fragment of human C2GnT-M that includes amino acid residues 34 to 438 of SEQ ID NO: 2. A functional fragment of C2GnT-M can also contain at least a part of either or both of the amino acid sequences designated SEQ ID NO: 10 and SEQ ID NO: 14.

C2GnT-M or a functional fragment of the invention can include, if desired, additional amino acid residues at the N- or C-terminus that facilitate its expression, secretion or purification. An example of a C2GnT-M functional fragment having additional amino acid residues is the chimeric C2GnT-M catalytic domain fragment described in Example II as including a signal peptide and IgG binding domain of protein A. Similarly, a functional fragment containing epitope sequences or sequences that direct the secretion or subcellular localization of C2GnT-M are also contemplated.

Functional fragments of C2GnT-M can also be produced, for example, by enzymatic or chemical cleavage of C2GnT-M. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990), which is incorporated herein by reference). Furthermore, functional fragments and derivatives of C2GnT-M can be produced by chemical synthesis. If desired, such as to optimize their functional activity, selectivity, stability or bioavailability, such molecules can be modified to include D-stereoisomers, non-naturally occurring amino acids, and amino acid analogs and mimetics. Examples of modified amino acids and their uses are presented in Sawyer, *Peptide Based Drug Design*, ACS, Washington (1995) and Gross and Meienhofer, *The Peptides: Analysis, Synthesis, Biology*, Academic Press, Inc., New York (1983), both of which are incorporated herein by reference.

The functional activity of C2GnT-M or a fragment or derivative, selected and prepared as described above, can be qualitatively or quantitatively assayed by a variety of in vitro and in vivo assays known in the art or described herein. For example, C2GnT-M and its fragments and derivatives can be assayed in vitro for core 2, core 4 and I branching activity using specific acceptor molecules and radiolabeled UDP-GlcNAc, as described in Example II, below, and the reaction products identified. Furthermore, antibodies selective for core 2, core 4 or I branched oligosaccharides can be used to assay the biological activities of C2GnT-M and its fragments and derivatives in vivo, as described in Example II, below.

The invention also provides a substantially pure C2GnT-M peptide having at least 10 amino acids, more preferably at least 20 amino acids, most preferably at least 50 amino acids characteristic of C2GnT-M, wherein the peptide is immunogenic. Such an immunogenic peptide can be used to produce antibodies specifically reactive with C2GnT-M or a fragment or derivative thereof.

A peptide of the invention that is characteristic of C2GnT-M can be chosen from a region of C2GnT-M that is not substantially homologous to other glucosaminyltransferases such as C2GnT-L and IGnT. Regions of high homology between human C2GnT-M, C2GnT-L and IGnT are boxed in FIG. 5. A peptide that is characteristic of C2GnT-M can be chosen to have less than 80% identity with C2GnT-L or IGnT, more preferably less than 70% identity with C2GnT-L or IGnT, most preferably less than 60% identity with C2GnT-L or IGnT. For example, an immunogenic peptide can contain substantially the amino acid sequence of at least a part of the amino acid sequences designated SEQ ID NO: 2, SEQ ID NO: 10 or SEQ ID NO: 14.

Peptides characteristic of C2GnT-M that are likely to be immunogenic can be determined using methods and algorithms known in the art and described, for example, by Margaht et al., *J. Immunol.* 138:2213–2229 (1987) and by Rothbard et al., *EMBO J.* 7:93–100 (1988), which are incorporated herein by reference. Immunogenicity of peptides of the invention can be screened by methods known in the art, such as assay of a delayed-type hypersensitivity response in a sensitized animal, or the elicitation of specific antibodies, as measured by an ELISA assay. Such peptides, if desired, can be conjugated to a carrier, such as KLH, serum albumin, tetanus toxoid and the like, using standard linking techniques. Additionally, such peptides can be formulated with an adjuvant known in the art, such as Freund's complete or incomplete adjuvant.

The invention also provides a method of modifying an acceptor molecule by contacting the acceptor molecule with a substantially pure C2GnT-M or functional fragment or derivative thereof under conditions that allow addition of core 2, core 4 or I GlcNAc to the acceptor. An acceptor molecule useful in the method can have, for example, a core 1 structure, Galβ1→3GalNAcα→R, which can be modified by a C2GnT-M activity to form a core 2 structure. An acceptor molecule can additionally or alternatively have a core 3 structure, GlcNAcβ1→3GalNAcα→R, which can be modified by a C2GnT-M activity to form a core 4 structure. Likewise, an acceptor molecule can have an i antigen structure,
Galβ1→4GlcNAcβ1→3Galβ1→4GlcNAcβ1→6Manα1→6Manβ→R' or GlcNAcβ1→3Galβ1→4GlcNAcβ1→6Manα1→Manβ1→R', which can be modified by a C2GnT-M activity to form an I antigen structure. An acceptor molecule that is particularly useful has a serine/threonine residue of a peptide or polypeptide as the "R" group.

Advantageously, the method of modifying an acceptor molecule by contacting the molecule with C2GnT-M can be used to prepare modified acceptor molecules that act as therapeutic agents to mimic or compete with oligosaccharides involved, for example, in cell proliferation, immune recognition, differentiation, adhesion or invasion, in order to modulate these processes. Such therapeutic agents can be administered to an individual in an effective amount, together with a pharmaceutically acceptable carrier, if desired. These therapeutic agents can be administered to an individual, either alone or in conjuction with conventional therapies such as surgery, immunosuppression, chemotherapy and radiation.

As an example of a contemplated application of the method, a molecule that forms an E-, P- or L-selectin ligand when contacted with C2GnT-M, either alone or in conjuction with additional glycosylases, can be used as an acceptor molecule of the invention to prepare a therapeutic agent for the treatment of cancer, inflammation or transplant rejection. Such modified acceptor molecules can be administered to an individual in an effective amount, for example, to inhibit the interaction between a cell and a selectin, or act as a selectin agonist to stimulate selectin-mediated signal transduction.

Appropriate acceptor molecules to prepare modified acceptor molecules include, for example, leukosialin, LAMPs, CEA-like proteins, LFA-1, GlyCAM-1, CD34, ESL-1, PSGL-1 and related molecules, which are described in Varki, *J. Clin. Invest.* 99:158–162 (1997), incorporated herein by reference. Other appropriate acceptor molecules include peptides, glycoproteins, glycolipids, and synthetic small molecules capable of accepting the transfer of a GlcNAc residue when contacted with C2GnT-M.

The invention provides a substantially pure nucleic acid molecule comprising substantially the nucleic acid sequence designated SEQ ID NO: 1, or the complement thereof. The invention also provides a substantially pure nucleic acid molecule encoding C2GnT-M or a functional fragment or derivative thereof, or the complement thereof, wherein C2GnT-M is characterized as a polypeptide having core 2, core 4 and I branching β-1→6-N-acetylglucosaminyltransferase activities. The nucleic acid molecule can encode a full-length C2GnT-M polypeptide, such as the human C2GnT-M cDNA shown in FIG. 4 (SEQ ID NO: 1). If desired, the nucleic acid molecule can encode a functional fragment of C2GnT-M, such as amino acid residues 34–438 of SEQ ID NO: 2. Additionally, the nucleic acid molecule can encode a polypeptide comprising substantially the amino acid sequence designated SEQ ID NO: 10 or SEQ ID NO: 14. Also contemplated are nucleic acid molecules that encode derivatives of C2GnT-M or functional fragments thereof.

Nucleic acid molecules of the invention can have the sequence of SEQ ID NO: 1 or of a native C2GnT-M encoding nucleic acid, but may also include minor substitutions, additions or deletions compared to the native sequence, such that they hybridize under relatively stringent conditions with the native sequence.

Nucleic acid molecules encoding C2GnT-M or any desired functional fragment or derivative thereof, or having substantially the sequence of SEQ ID NO: 1, can be produced or isolated by methods known to those skilled in the art. For example, the polymerase chain reaction (PCR), or reverse-transcription PCR (RT-PCR), can be used to produce a nucleic acid molecule having any desired boundaries. Such nucleic acid molecules can be amplified exponentially starting from as little as a single gene copy by means of PCR. Other methods of producing a substantially pure nucleic acid molecule encoding C2GnT-M include, for example, using antibodies of the invention to screen an expression library. Additionally, a cDNA or genomic library can be screened using nucleic acid molecules or oligonucleotides corresponding to or complementary to a C2GnT-M sequence as hybridization probes. Alternatively, the nucleic acid molecules of the invention can be chemically synthesized by methods known in the art including, for example, the use of an automated nucleic acid synthesizer. Desired fragments of a C2GnT-M nucleic acid can be produced, for example, by restriction enzyme digestion or mild DNAse digestion of a longer C2GnT-M molecule, and purification of the resulting fragments.

If desired, a nucleic acid molecule of the invention can incorporate a detectable moiety such as a radiolabel, a fluorochrome, a ferromagnetic substance, a luminescent tag or a detectable binding agent such as biotin. These and other detectable moieties and methods of incorporating such moieties into a nucleotide sequence are well known in the art and are commercially available. A population of labeled nucleic acid sequences can be prepared, for example, by nick translation of a nucleic acid molecule of the invention or by 3' or 5' end labeling using methods known in the art.

A detectably labeled nucleic acid molecule of the invention can be used in hybridization assays, such as Southern or northern blots, screening genomic or cDNA libraries, solution hybridization and in situ hybridization to cell or tissue samples. Hybridization assays using detectably labeled nucleic acid molecules can be advantageously used, for example, to determine the chromosomal location of C2GnT-M or to assay whether a C2GnT-M gene is mutated, amplified or translocated in chromosomes of a particular sample. Additionally, hybridization assays with a detectably labeled nucleic acid molecule of the invention can be used to determine the level of expression of C2GnT-M RNA in a cell or tissue sample. An example of the use of a detectably labeled nucleic acid molecule of the invention is provided in Example IV, below. The required stringency of hybridization conditions depend, for example, on the detergent and salt concentration and hybridization temperature, and can be determined for a particular application by those skilled in the art.

Altered C2GnT-M expression in a sample, such as increased or decreased C2GnT-M expression compared to a control sample, can indicate a pathology or increased risk of a pathology such as, for example, tumor invasion and metastasis, transplant rejection, or an immune-related disorder, such as an autoimmune disease or an immunodeficiency. Mutation of the C2GnT-M gene, or translocation of the 15q22.1 chromosomal region where C2GnT-M maps, can also be diagnostic or prognostic indicators of such pathologies.

The invention also provides substantially pure nucleic acid molecules operatively linked to a promoter of RNA transcription. Such operatively linked nucleic acid molecules can be used for transcribing RNA in vitro or in vivo. Useful promoters can direct transcriptional activity from a DNA-dependent RNA polymerase, which is known generally in the art as RNA polymerase, or from an RNA-dependent RNA polymerase, such as SP6, T4 and T7 RNA polymerase. One skilled in the art recognizes that a particular RNA polymerase requires a specific transcriptional start site, such as a TATA sequence or, for example, an SP6 promoter. Methods for operatively linking a nucleic acid to a promoter are well known in the art and include, for example, cloning the nucleic acid into a vector containing a suitable promoter or appending the promoter to a linear nucleic acid sequence using PCR.

The invention also provides a vector containing an isolated nucleic acid molecule encoding a C2GnT-M or a functional fragment or derivative thereof. Contemplated vectors include those derived from a virus, such as a bacteriophage, a baculovirus or a retrovirus, and vectors derived from bacteria or a combination of bacterial and viral sequences, such as a cosmid or a plasmid. The vectors of the invention can advantageously be used to clone or express a C2GnT-M, functional fragment or derivative of the invention.

A nucleic acid molecule can be inserted into a cloning or expression vector using any of several methods well known in the art. For example, a nucleic acid molecule to be inserted and a vector into which the molecule is to be inserted can be treated with a restriction enzyme, which creates complementary ends on the molecule and the vector, thus allowing the ends to base pair with each other and further allowing the nucleic acid molecules to be covalently linked using, for example, a DNA ligase. Alternatively, the nucleic acid molecule to be inserted can have ligated thereto synthetic nucleic acid linkers that correspond to a restriction site in the vector DNA. Following treatment of the DNA molecules with the appropriate restriction endonuclease, the sequences can be joined as described above.

A vector also can contain an oligonucleotide encoding, for example, a termination codon or other transcription or translation regulatory elements. The vector also can contain other appropriate restriction sites, which can be used for inserting other useful nucleic acid molecules including, but not limited to a selectable marker gene, such as the neomycin or hygromycin resistance gene, which is useful for selecting stable or transient transfectants in mammalian cells; enhancer sequences and promoter sequences, which are obtained, for example, from a viral, bacterial or mammalian gene; transcription termination and RNA processing signals, which are obtained from a gene or a virus such as SV40, such sequences providing, for example, stability of a transcribed mRNA sequence; an origin of replication obtained, for example, from SV40, polyoma or E. coli, which allow for proper episomal replication; versatile multiple cloning sites; and RNA promoters such as the above-described T7 and SP6 promoters, which allow for in vitro transcription of sense and antisense RNA.

Contemplated vectors include vectors that provide for expression in a host cell such as a bacterial cell, a yeast cell, an insect cell, a mammalian cell and other animal cells. Such expression vectors include regulatory elements specifically required for expression of the DNA in a cell, the elements being located relative to the nucleic acid molecule encoding C2GnT-M so as to permit expression thereof. The regulatory elements can be chosen to provide constitutive expression or, if desired, inducible or cell type-specific expression. Regulatory elements required for expression have been described above and include transcription and translation start sites and termination sites. Such sites permit binding, for example, of RNA polymerase and ribosome subunits. A bacterial expression vector can include, for example, an RNA transcription promoter such as the lac promoter, a Shine-Delgarno sequence and an initiator AUG codon in the proper frame to allow translation of an amino acid sequence.

Similarly, a eucaryotic expression vector can include, for example, a heterologous or homologous RNA transcription promoter for RNA polymerase binding, a polyadenylation signal located downstream of the coding sequence, an AUG start codon in the appropriate frame and a termination codon to direct detachment of a ribosome following translation of the transcribed mRNA. Vectors having these and other characteristics are commercially available or are assembled by those skilled in the art using well known methods. An example of a eukaryotic expression vector of the invention is pcDNA3-A-C2GnT-M, described in Example I, below.

The invention also provides a host cell containing a vector that expresses a nucleic acid molecule encoding C2GnT-M or a functional fragment or derivative thereof. Such host cells can be used to express and isolate substantially pure recombinant C2GnT-M, using biochemical procedures described above. Additionally, the host cells of the invention can be used in in vitro or in vivo methods to effectively modify core 2, core 4 or I branches on acceptor molecules. If desired, such host cells can be chosen or transfected so as to co-express one or more additional enzymes involved in oligosaccharide biosynthesis, such as a sialyltransferase or fucosyltransferase. Therefore, such host cells can be used to prepare acceptor molecules having high affinity for glycoprotein receptors, such as ligands for E-, P- and L-selectins, as described above.

Host cells expressing C2GnT-M can also be used to screen for selective inhibitors of C2GnT-M or for agents that selectively react with core 2, core 4 or I-branched oligosaccharides. These agents can be administered to an individual to prevent or treat pathologies related to aberrant expression of C2GnT-M or of core 2, core 4 or I-branched oligosaccharides.

Examples of useful host cells include bacterial, yeast, frog and mammalian cells. Various mammalian cells useful as host cells include, for example, mouse NIH/3T3 cells, CHO cells, COS cells and HeLa cells. In addition, mammalian cells obtained, for example, from a primary explant culture are useful as host cells. Host cells that are specificaly contemplated are non-human mammalian embryonic stem cells, fertilized eggs and embryos, which can be routinely used to generate transgenic animals, such as mice, which express C2GnT-M in some or all of their cells. Transgenic mice expressing C2GnT-M can be used to study the normal and pathological role of this enzyme and also to screen for compounds that enhance or inhibit its activity.

Methods for introducing a vector into a host cell are well known in the art and include, for example, various methods of transfection such as the calcium phosphate, DEAE-dextran and lipofection methods, as well as electroporation and microinjection. An example of a host cell of the invention is a CHO cell transfected with the pcDNA3.1-C2GnT-M vector, as described in Example II, below.

The methods of nucleic acid cloning and expression described herein are routine in the art and are described, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1989). These references and the publications cited therein are hereby incorporated by reference.

The invention also provides a substantially pure oligonucleotide having a nucleotide sequence corresponding to or complementary to at least 15 nucleotides from SEQ ID NO: 1, SEQ ID NO: 9 or SEQ ID NO: 13. Also contemplated is a substantially pure oligonucleotide having a nucleotide sequence corresponding to or complementary to at least 20 nucleotides from SEQ ID NO: 1, SEQ ID NO: 9 or SEQ ID NO: 13 such as, for example, at least 30 nucleotides therefrom, or preferably at least 40 nucleotides therefrom. Such oligonucleotides can advantageously be used, for example, as primers for PCR, or sequencing, as probes for research or diagnostic applications, and in therapeutic applications. For example, as described above in regard to a nucleic acid molecule of the invention, an oligonucleotide of the invention can incorporate a detectable moiety such as a radiolabel, a fluorochrome, a ferromagnetic substance, a luminescent tag or a detectable binding agent such as biotin, and used to detect expression of C2GnT-M RNA in a cell or tissue. Those skilled in the art can determine the appropriate length and nucleic acid sequence of a C2GnT-M oligonucleotide for a particular application.

An oligonucleotide of the invention can be particularly useful in therapeutic applications to reduce, inhibit or prevent expression of C2GnT-M protein. For example, an antisense molecule, which can be DNA or RNA, can be targeted to all or a portion of the 5'-untranslated region or of the 5'-translated region of a C2GnT-M nucleic acid sequence in a cell. Such antisense molecules can be synthesized using nucleotide analogs, or non-natural nucleotide linkages, which confer desirable characteristics on the oligonucleotides such as nuclease resistance.

Figure 4A:
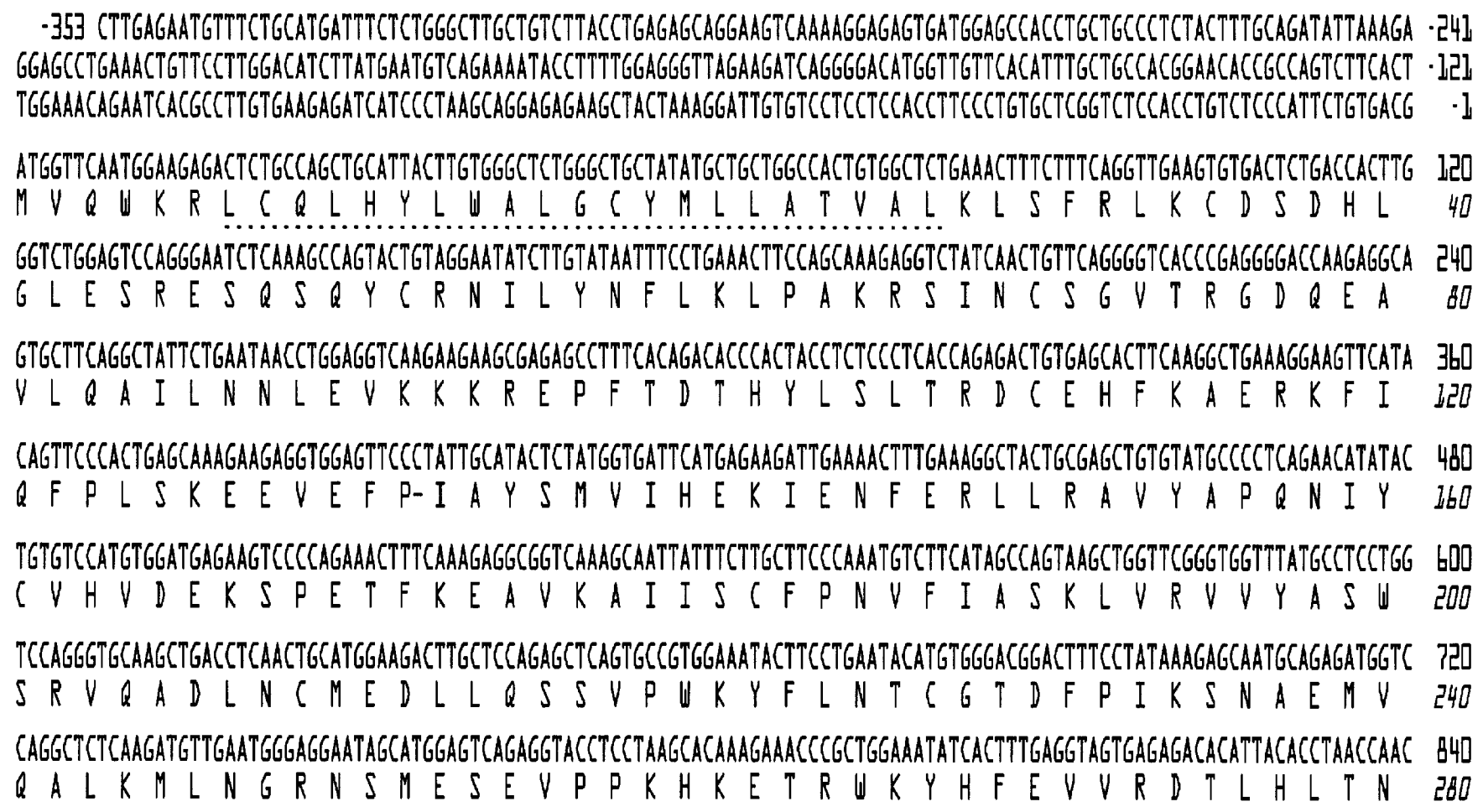

An oligonucleotide of the invention can be complementary to at least a portion of the C2GnT-M nucleic acid sequence shown in FIG. 4 (SEQ ID NO: 1). Since the 5'-region of a nucleic acid contains elements involved in the control of expression of an encoded protein, an antisense oligonucleotide directed to the 5'-region of a nucleic acid molecule can reduce the levels of protein expressed in a cell, by reducing either transcription or translation of the nucleic acid. Thus, an antisense oligonucleotide is useful as a drug to inhibit expression of C2GnT-M in a patient, where the patient's symptoms are related to overexpression of C2GnT-M or to aberrant expression of core 2, core 4 or I oligosaccharides.

An antisense oligonucleotide that effectively reduces expression of C2GnT-M can be administered to an individual in an effective amount in a pharmaceutical composition together with a pharmaceutically acceptable carrier. A pharmaceutical composition can include, for example, a vehicle such as a hydrophobic carrier molecule that facilitates introduction of the oligonucleotide through a cell membrane and specific binding with a nucleic acid encoding a C2GnT-M present in the cell. A liposome is an example of a hydrophobic carrier molecule. However, a pharmaceutically acceptable carrier also can be a structure, such as a ligand, that is recognized and bound by a particular cell surface receptor, which can be specific for a selected cell type into which one wishes to introduce the oligonucleotide.

Using knowledge of the human C2GnT-M nucleic acid sequence described herein (SEQ ID NO: 1), one skilled in the art can readily clone C2GnT-M-encoding nucleic acids from other mammalian species using conventional library screening methods or using the polymerase chain reaction (PCR). For example, nucleic acid molecules encoding mouse C2GnT-M were isolated using human PCR primers to amplify mouse genomic DNA, as described in Example V. These nucleic acid molecules can be used to express recombinant C2GnT-M protein or to generate animals lacking one or both copies of the C2GnT-M gene. For example, mouse C2GnT-M genomic DNA can be incorporated into a gene-targeting vector. The gene targeting vector can be introduced into mouse embryonic stem cells and used to generate C2GnT-M deficient mice, using analogous methods as those described in Ellies et al., *Immunity* 9:1–20 (1998) for generating C2GnT-L deficient mice. C2GnT-M deficient mice can be used to study the normal and pathological role of this enzyme and also to screen for compounds that enhance or inhibit its activity.

The invention also provides an antibody or antigen binding fragment thereof specifically reactive with C2GnT-M or with a functional fragment or derivative thereof, wherein C2GnT-M is characterized as a polypeptide having core 2, core 4 and I branching $\beta$-1-6-N-acetylglucosaminyltransferase activity. Such antibodies can be used, for example, to detect the expression of C2GnT-M in a sample or to affinity purify C2GnT-M from a composition. Also contemplated is the use of such antibodies to selectively target cells that express C2GnT-M, so as to alter expression of C2GnT-M. If desired, antibodies can be administered to an individual in conduction with a cytotoxic or cytostatic moiety in order to neutralize or kill cells expressing C2GnT-M.

An antigen binding fragment of an antibody of the invention includes, for example, individual heavy or light chains and fragments thereof, such as VL, VH and Fd; monovalent fragments, such as Fv, Fab, and Fab'; bivalent fragments such as F(ab')$_2$; single chain Fv (scFv); and Fc fragments. Antigen binding fragments include, for example, fragments produced by protease digestion or reduction of a C2GnT-M antibody, as well as fragments produced by recombinant DNA methods known to those skilled in the art.

The antibodies of the invention can be produced by any method known in the art, and can be polyclonal or monoclonal. For example, a C2GnT-M polypeptide or immunogenic peptide of the invention, or a vector expressing such a polypeptide, can be administered to an animal, using standard methods, and the antibodies isolated. The antibodies can be used in the form of serum isolated from an immunized animal or the antibody can be purified from the serum. Additionally, the antibodies can be produced by a hybridoma cell line, by chemical synthesis or by recombinant methods. Modified antibodies such as chimeric antibodies, humanized antibodies and CDR-grafted or bifunctional antibodies can be produced by methods well known to those skilled in the art and, therefore, are considered to be within the contemplated invention.

Where the antibodies are used for detecting C2GnT-M, detection can be in vitro as in a diagnostic assay of a sample obtained from a subject or in vivo for imaging the localization of C2GnT-M in a subject. Immunological procedures useful for in vitro detection of a target C2GnT-M protein or peptide in a sample include immunoassays that employ a detectably labeled antibody. Such immunoassays include, for example, ELISA, Pandex microfluorimetric assay, agglutination assays, flow cytometry, serum diagnostic assays and immunohistochemical staining procedures. These and other methods are well known in the art and described, for example, by Harlow and Lane (1988).

An antibody can be labeled with a detectable moiety so as to be detectable using various methods. For example, a detectable moiety can be directly or indirectly attached to the antibody. Useful detectable moieties include, for example, enzymes, fluorogens, chromogens and chemiluminescent labels.

Methods of preparing and using antibodies and antigen-binding fragments, including detectably labeled antibodies, are described, for example, in Harlow and Lane, *Antibodies: A Laboratory Manual,* Cold Spring Harbor Laboratory, New York (1989); in Day, E. D., *Advanced Immunochemistry,* Second Ed., Wiley-Liss, Inc., New York, N.Y. (1990); and in Borrebaeck (Ed.), *Antibody Engineering,* Second Ed., Oxford University Press, New York (1995), which are incorporated herein by reference.

It is understood that modifications that do not substantially affect the activity of the various embodiments of this invention are also included within the definition of the invention provided herein. Accordingly, the following examples are intended to illustrate but not limit the present invention.

EXAMPLE I

Isolation of cDNA encoding C2GnT-M

This example shows the isolation and characterization of a cDNA encoding human C2GnT-M.

Comparison of cloned C2GnT and IGnT demonstrated that there are three regions highly shared by these two members of the β-1-6-N-acetylglucosaminyltransferase gene family, as described in Bierhuizen et al. *Genes Dev.* 7:468–478 (1993), incorporated herein by reference. The coding sequences of human C2GnT and IGnT homologous region A (nucleotides 315–702 for C2GnT-L and nucleotides 252–618 for IGnT) were therefore used to search dbEST using the TBLASTN program. The human C2GnT and IGnT sequences are reported in Bierhuizen et al. *Proc. Natl. Acad. Sci. USA* 89:9326–9330 (1992), and Bierhuizen et al. *Genes Dev.* 7:468–478 (1993), respectively, incorporated herein by reference in their entirety. A single query gene (AA307800) of 554 bp was found to have 67% and 62% identity with the coding regions of C2GnT and IGnT, respectively.

In order to obtain a full-length cDNA, 5'-RACE and 3'-RACE reactions were performed. Human fetal brain Marathon Ready cDNA was used as a template to obtain both the 5'- and 3'-sequence. 5'-RACE and 3'-RACE were separately carried out by PCR using anti-sense primer or sense primer and AP1 adapter (CLONTECH). The anti-sense and sense primers used were CCL2AS, 5'-CCAGCTTACTGGCTATGAAGACATTTGG-3' (SEQ ID NO: 5) and CCL1, 5'-GAGCACTTCAAGGCTGAAAGGAAGTTC-3' (SEQ ID NO: 6). These primers were designed to have 247 bp-overlapping sequence between these two RACE products. PCR products were cloned into pCR2.1-TOPO (Invitrogen) and colony hybridization was performed to identify the RACE products using 32P-labeled DNA fragment of 247 bp, obtained by PCR using CCL1 and CCL2AS primers described above. The nucleotide sequence was identical among several clones examined.

Based on the obtained sequences, a cDNA was prepared by RT-PCR of poly(A)+ RNA from HT-29 colonic carcinoma cells and the sequence of genomic DNA was analyzed by PCR. RT-PCR was carried out as described in Angata et al., *J. Biol. Chem.* 273:28524–28532 (1998), incorporated herein by reference, except that Thermoscript™ (Gibco BRL) was used. Since the two nucleotide sequences were found to be identical, the cDNA obtained by the above RT-PCR was thus cloned into pcDNA3.1/Zeo(-) vector, resulting in pcDNA3.1-C2GnT-M.

The full-length cDNA obtained encodes an open reading frame of 1314 base pairs, predicting a protein of 438 amino acid residues (50,863 Da) which was subsequently designated C2GnT-M. The nucleotide sequence of C2GnT-M (SEQ ID NO: 1) and predicted amino acid sequence of C2GnT-M (SEQ ID NO: 2) are presented in FIG. 4. A hydropathy plot predicts that this protein has a type II membrane topology seen for almost all mammalian glycosyltransferases so far cloned, as described in Paulson et al., *J. Biol. Chem.* 268:17615–17618 (1989), incorporated herein by reference.

The amino acid sequence of C2GnT-M has 48.2% and 33.8% identity with that of C2GnT-L and IGnT, respectively, indicating that newly cloned C2GnT-M is related more closely to C2GnT-L than to IGnT. The alignment of the amino acid sequences of human C2GnT-M (SEQ ID NO: 2), C2GnT-L (SEQ ID NO: 3) and IGnT (SEQ ID NO: 4) are presented in FIG. 5. The amino acid residues are numbered with respect to the translation initiation methionine. Identical residues are indicated by boxes. The regions A, B and C are designated after comparison of all three proteins using a Clustal program. Dots denote gaps in the sequence. In particular, the amino acid sequence of C2GnT-M is highly homologous to that of C2GnT-L in three regions in the catalytic domain; both share 72.1%, 57.7% and 75.0% identity in A, B and C regions, respectively. The A, B and C regions of the three proteins are indicated in FIG. 5.

There are two potential N-glycosylation sites in the C2GnT-M sequence, as indicated by the asterisks in FIG. 4. A consensus sequence for polyadenylation signal is present at nucleotides 1747–1752, as indicated by the underlined sequence in FIG. 4, followed by a poly(A) tail. The signal/membrane-spanning domain is denoted by a dotted line. As indicated by the size of the mRNA (see Example IV), the isolated cDNA of 2128 base pairs appears to be full-length.

EXAMPLE II

Enzymatic activities of C2GnT-M

This example shows that C2GnT-M directs the expression of core 2 branched oligosaccharides and I antigens on the cell surface. This example further shows that C2GnT-M has core 2, core 4 and I branch enzyme activities.

C2GnT-M directs the expression of core 2 branched oligosaccharides and I antigens on the cell surface cDNAs encoding the catalytic domains of C2GnT-M, C2GnT-L and IGnT were expressed in CHO cells and the ability of these enzymes to direct the expression of core 2 branched oligosaccharides and I antigens on the cell surface were compared. The expression vector encoding chimeric C2GnT-M was prepared as follows. The cDNA fragment encoding a putative catalytic domain plus stem region was prepared by PCR using pcDNA3.1-C2GnT-M, described in Example I, as a template. The 5'-primer for the PCR contained the sequence of BglII site and nucleotides 99–124 (nucleotides 1–3 encode the initiation methionine) while the 3'-primer contained 3'-end of the coding sequence, stop codon and XbaI site. The cDNA fragment encoding amino acid residues 34–438 of C2GnT-M was ligated into the BamHI and XbaI sites of pcDNA3-A harboring a cDNA encoding a signal peptide and IgG binding domain of protein A, as described by Angata et al., *J. Biol. Chem.* 273:28524–28532 (1998), incorporated herein by reference, resulting in pcDNA3-A·C2GnT-M.

Similarly, the catalytic domain of IGnT (amino acid residues 30–400) was cloned into pcDNAI-A (Angata et al., supra, (1998)), resulting in pcDNAI-A·IGnT. pcDNAI-A·C2GnT-L was constructed as described in Bierhuizen et al. supra, (1992) except that the vector pcDNAI-A (Angata et al., supra, (1998)) was used.

CHO cells were transiently transfected with pcDNAI-C2GnT-L, pcDNA3.1-C2GnT-M, or pcDNAI-IGnT and the expression of core 2 branched oligosaccharides and I antigen were detected by T305 antibody followed by fluorescein isothiocyanate (FITC)-conjugated goat-anti-mouse IgG, or by anti-I serum (Ma) followed by FITC-conjugated anti-human IgM, respectively, as described in Bierhuizen et al. supra (1992), and Bierhuizen et al. supra (1993). T305 reacts with core 2 oligosaccharides expressed in leukosialin (Bierhuizen et al. supra (1992); Bierhuizen et al., *J. Biol. Chem.* 269:4473–4479 (1994), incorporated herein by reference). Therefore, for T305 staining, the cells were co-transfected with pcDSRa-leukosialin and cDNA encoding the glycosyltransferases.

Figure 6:
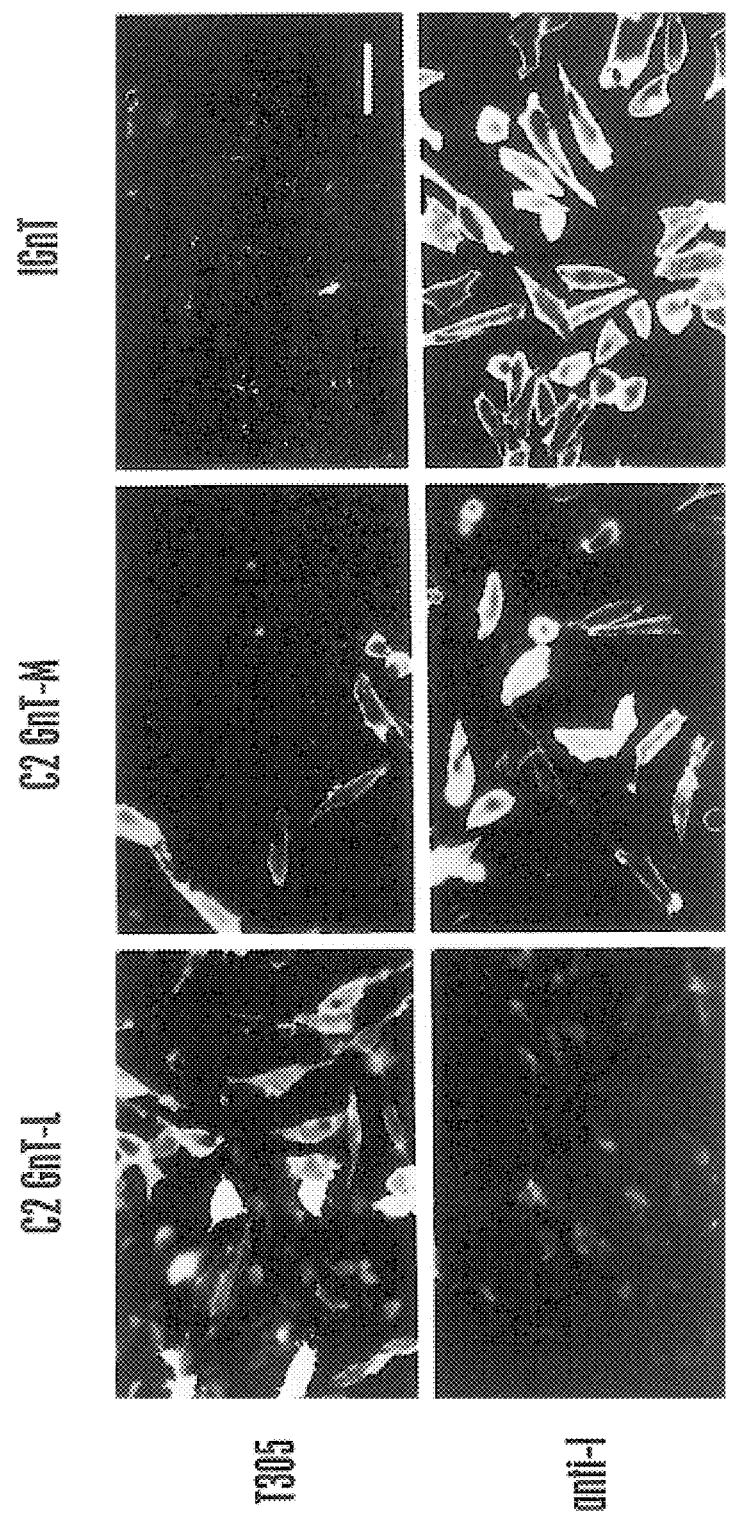
FIG. 6 shows immunofluorescent staining of CHO cells transfected with pcDNAI-C2GnT-L (C2GnT-L), pcDNA3.1-C2GnT-M (C2GnT-M) or pcDNAI-IGnT (TGnT), using T305 monoclonal antibody or anti-I human serum. Bar=40 µm.

Since C2GnT-M is highly homologous to C2GnT-L and IGnT, the ability of C2GnT-M to direct the expression of core 2 branched oligosaccharides and I antigen on the cell surface was tested. After transfecting CHO cells with pcDNAI-C2GnT-L or pcDNA3.1-C2GnT-M together with a leukosialin cDNA, the cells showed strong staining with T305 antibody, as shown in FIG. 6. In contrast, no staining was observed when CHO cells were transfected with pcDNAI-IGnT under the same conditions (FIG. 6, upper right panel). After transfecting CHO cells with pcDNA3.1-C2GnT-M and pcDNAI-IGnT, respectively, the cells were moderately and strongly stained with anti-I antibody, as shown in FIG. 6. The I antigen was not, however, expressed after transfecting cells with pcDNAI-C2GnT-L, as shown in FIG. 6, lower left panel.

These results indicate that C2GnT-M has the property of having the activities of both core 2 and I branching enzymes, which is distinct from the properties of either C2GnT-L or IGnT.

C2GnT-M has core 2, core 4 and I branch enzyme activities

In order to determine the core 2, core 4 and I branch enzyme activities of C2GnT-M, in comparison to C2GnT-L and IGnT, pcDNA3-A·C2GnT-M, pcDNAI-A·C2GnT-L or pcDNAI-A·IGnT was transiently transfected into CHO cells as described in Ong et al., *J. Biol. Chem.* 273:5190–5195 (1998), incorporated herein by reference. Twenty four hours after the transfection, the medium was replaced with serum free Opti-MEM (Gibco) and cultured for an additional 48 h. The spent medium obtained was then concentrated by Centriprep 30 (Amicon) and directly used for C2GnT-L and IGnT assays. For assaying C2GnT-M, the chimeric enzyme was adsorbed to IgG-Sepharose from the concentrated spent medium and the enzyme bound to IgG-Sepharose was used as the enzyme source as described in Nakayama et al., *J. Biol. Chem.* 271:1829–1832 (1996). The enzyme incubation mixture contained 1 mM acceptor, 100 mM GlcNAc, 50 mM D-galactonic acid γ-lactone, 10 mM EDTA, 1 mM UDP-GlcNAc containing 0.5 µCi of UDP-[$^3$H]GlcNAc, 20 µl of the enzyme solution in total of 50 µl 50 mM MES, pH 7.0. After incubation at 37° C. for 1 h, the reaction was stopped by diluting with 1 ml of water and reaction products were purified by a C18 reversed-phase column (Alltech) as described in Ujita et al., *J. Biol. Chem.* 273:34843–34849, (1999)

CHO cells transfected with pcDNAI-A vector were used as a negative control and the radioactivity obtained was subtracted from the radioactivity obtained in experiments with each enzyme. Since CHO cells contain no C2GnT or IGnT activity (Bierhuizen et al. supra (1992); Bierhuizen et al. supra (1993); Sasaki et al., *J. Biol. Chem.* 262:12059–12076 (1987); Smith et al., *J. Biol. Chem.* 265:6225–6234 (1990), each of which is incorporated herein by reference), the radioactivity obtained in mock experiments was less than 0.1% of the radioactivity incorporated in the reactions with the highest incorporation.

As acceptors, Galβ1→3GalNAcα→pNP and GlcNAcβ1→3GalNAcypNP (Toronto Chemicals) were used for assaying C2GnT and C4GnT activity, respectively. Galβ1→4GlcNAcβ1→3 Galβ1→4GlcNPcβ1→6Manα1→6Manβ-octyl, and GlcNAcβ1→3 Galβ1→4GlcNAcβ1→6Manα1→Manβ1→octyl were used for assaying IGnT activity. Since addition of N-acetylglucosamine takes place at the underlined galactose residues, the two acceptors serve for centrally acting IGnT (cIGnT) and predistally acting IGnT (dIGnT), respectively, as described by Gu et al., *J. Biol. Chem.* 267:2994–2999 (1992), incorporated herein by reference. The octyl compounds were synthesized as described in Ujita et al., supra (1999) and provided by Drs. Joseph McAuliffe and Ole Hindsgaul of the Burnham Institute, La Jolla, Calif.

To identify the reaction products, the product obtained after C18 reversed-phase column chromatography was subjected to HPLC using a column (4×300 mm) of NH$_2$-bonded silica (Varian Micropak AX-5) equipped in Gilson 306. The column was eluted for 35 min with a linear gradient from the solvent A to a mixture of the solvent A (70%) and the solvent B (30%); the solvent A is composed of 80% acetonitrile and 20% 15 mM $KH_2PO_4$ in H2O while the solvent B is composed of 40% acetonitrile and 60% 15 mM $KH_2PO_4$ in $H_2O$.

Figure 7A:
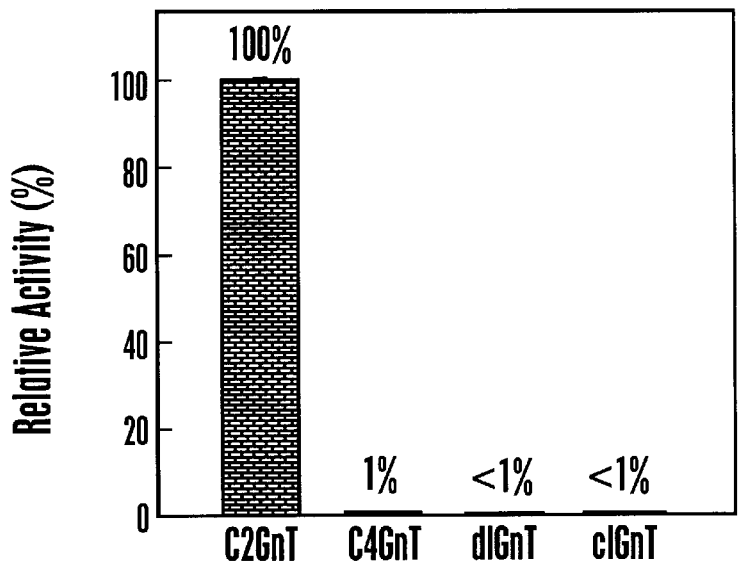
FIG. 7 shows the incorporation of $^3$H-GlcNAc from UDP-[$^3$H]GlcNAc into acceptor molecules following contact with C2GnT-L (A), C2GnT-M (B) and IGnT (C). The standard errors are shown by bars.

The highest activity of C2GnT-L, C2GnT-M and IGnT were 30 nmoles/h/ml (for C2GnT activity), 130 pmoles/h/ml (for C2GnT activity), and 894 pmoles/h/ml (for cIGnT activity), respectively, and they were taken as 100%. As shown in FIG. 7A, C2GnT-L exhibited a strong activity toward Galβ1→3GalNAcα→pNP and a barely detectable amount of activity toward GlcNAcβ1→3GalNAcα→pNP. As expected C2GnT-L did not show any activity toward acceptors for IGnT. The recombinant IGnT exhibited strong activity as a cIGnT as shown previously by Mattila et al., *J. Biol. Chem.* 273:27633–27639 (1998), but also moderate activity as a dIGnT and very weak activity as a C4GnT, as shown in FIG. 7C.

Figure 7B:
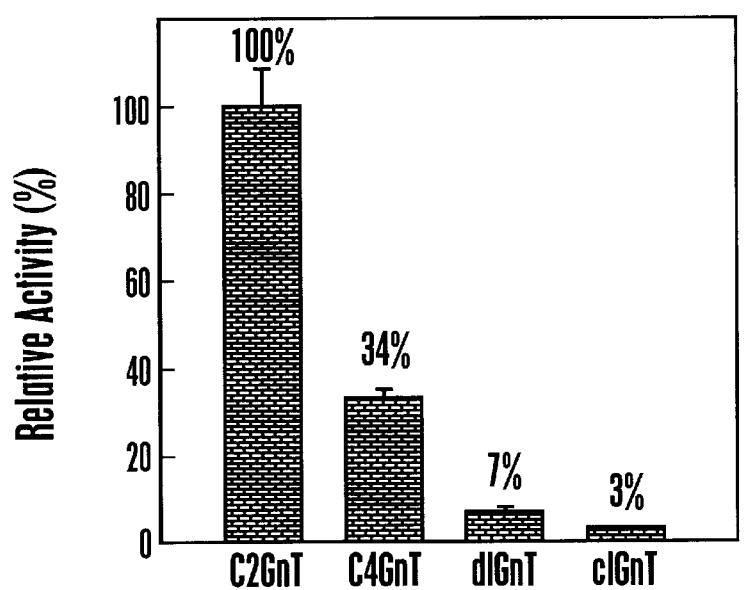
Figure 7C:
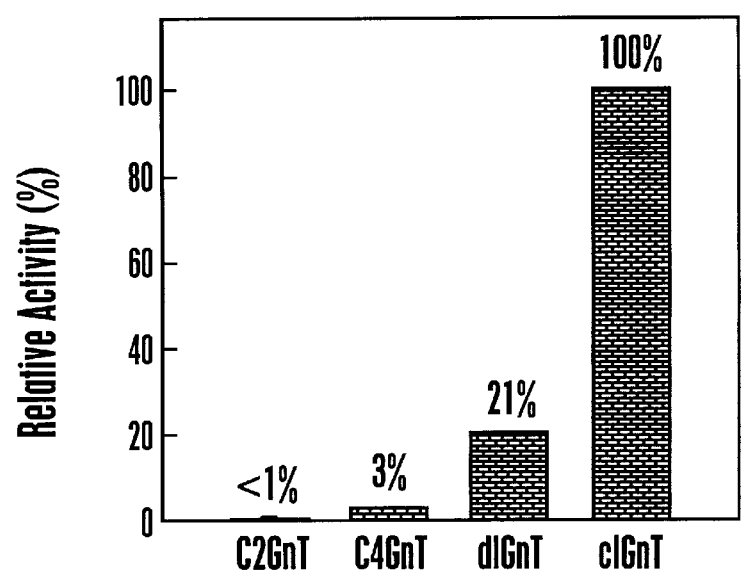

I branching enzyme activity of C2GnT-M was detected more as a dIGnT than a cIGnT, as shown in FIG. 7B. Although the presence of a dIGnT enzymatic activity was reported previously (Piller et al., *J. Biol. Chem.* 259:13385–13390 (1988); Brockhausen et al. supra (1986); Ropp et al. supra (1991); Gu et al., *J. Biol. Chem.* 267:2994–2999 (1992), each of which is incorporated herein by reference), a cDNA encoding an enzyme acting more as a dIGnT than as a cIGnT was not reported before. Furthermore, previously reported hog gastric mucosa (Piller et al., supra (1988)) and rat liver (Gu et al. supra (1992)) dIGnT activities had much less C2GnT or C4GnT activity compared to dIGnT activity, while the opposite is true for C2GnT-M. As compared to the bovine trachea C2GnT enzyme preparation reported by Ropp et al. supra (1991), in which dIGnT activity was almost 40% of its C2GnT activity, dIGnT activity in C2GnT-M described herein is only 7% of its C2GnT activity, although similar acceptors were used in both studies. In a study reported by Vavasseur et al., *Glycobiology* 5:351–357 (1995), incorporated herein by reference, the ratio of C2GnT and dIGnT activities in LS180, HT29 and NC 1498 colonic carcinomas was similar to that of C2GnT-M reported herein.

C2GnT-M also exhibited a substantial activity to GlcNAcβ1→3GalNAcα→pNP, indicating that C2GnT-M exhibits significant C4GnT activity (FIG. 7B) in addition to IGnT and C2GnT activities, indicating that a single enzyme can catalyze three different but related reactions.

EXAMPLE III

Chromosomal mapping of C2GnT-M gene

This example shows the chromosomal localization of the C2GnT-M gene.

DNA samples were prepared from a panel of human x rodent somatic cell hybrids containing human minichromosomes from 83 radiation hybrids of the Stanford Human Genome Center G3 RH panel (Cox et al., *Science* 250:245–250 (1990); Gebe et al., *J. Biol. Chem.* 272:6151–6158 (1997); both of which are incorporated herein by reference) (Research Genetics, Huntsville, Ala.). To determine the C2GnT-M locus, these DNA samples were analyzed by PCR using 5'-primer, 5'-TCAGGGGTCACCCGAGGGGACCAAG-3' (211–235) (SEQ ID NO: 7) and 3' primer, 5'-CTCCACCTCTTCTTTGCTCAGTGG-3' (367–390) (SEQ ID NO: 8). The PCR conditions were 10 cycles of 94° C. for 1 min, 60° C. for 1 min, and 72° C. for 30 sec followed by 25 cycles of 94° C. for 1 min, 63° C. for 1 min and 72° C. for 30 sec.

The maximum likelihood analysis was carried out by submitting the results to the RH server at the Stanford Genome Center, as described by Cox et al., supra (1990); Gebe et al., supra (1997). Similarly, chromosomal mapping was carried out on the C2GnT-L and IGnT genes using PCR and the Stanford Human Genome Center G3 RH panel. It was also obtained using 3'-EST mapping data from the National Center for Biotechnology Information.

This analysis placed the C2GnT-M gene between two chromosome markers D15S1160 and D15S1347, thus mapping the gene to q22.1 region of chromosome 15. Similar analysis placed the C2GnT-L gene and IGnT gene at q13 of chromosome 9 and at p24 of chromosome 6, respectively.

EXAMPLE IV

Expression of C2GnT-M transcripts

This example shows the expression of C2GnT-M and C2GnT-L transcripts in various human tissues and cancer cell lines.

Northern blots of multiple human tissues and cancer cell lines (CLONTECH) were hybridized with $^{32}$p-labeled cDNA fragments of pcDNAI-C2GnT-L and pcDNA3.1-C2GnT-M, as described by Ong et al., supra (1998). Each lane contained 2 μg of poly(A)+RNA. Each blot contained eight lanes and was run separately. The cDNA fragments were prepared by BamHI and PstI digestion (nucleotides—219 to 495) of C2GnT-L or by PCR (nucleotides 1 to 577 of C2GnT-M) using C2GnT-M cDNA as a template.

Figure 8:
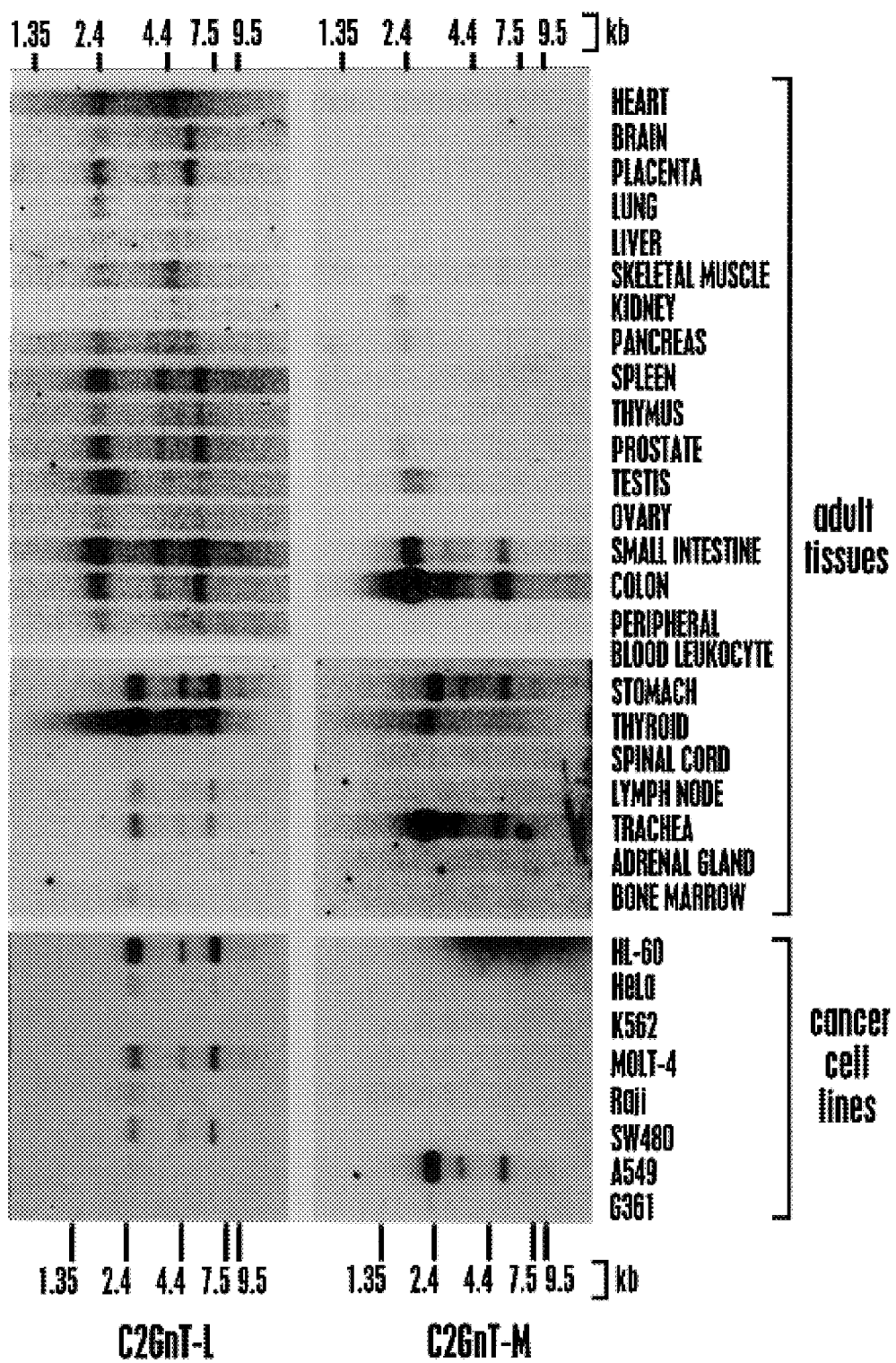
FIG. 8 shows Northern analysis of C2GnT-M and C2GnT-L expression in tissues and cell lines.

Northern blot analysis demonstrates that transcripts of C2GnT-M are predominantly expressed in colon, small intestine, trachea, stomach and thyroid, and are barely expressed in testis, prostate, kidney and pancreas, as shown in FIG. 8. Thus, C2GnT-M is likely involved in the synthesis of mucin-type oligosaccharides. It was recently demonstrated that a major glycoprotein in calf thyroid contains core 2 branched O-glycans and I-branched N-glycans (Edge et al., *Arch. Biochem. Biophys.* 343:73–80 (1997), incorporated herein by reference), indicating that thyroid synthesizes mucin-type O-glycans.

The transcripts of C2GnT-L, on the other hand, are more widely expressed and were detected also in heart, brain, placenta, spleen, peripheral leukocytes, lymph node and bone marrow, where the transcripts of C2GnT-M were not detected (FIG. 8). Moreover, the transcripts of C2GnT-L were detected in HL-60, MOLT-4, and Raji leukemic cell lines, colon adenocarcinoma SW480 and cervical carcinoma HeLa cells, where the transcripts of C2GnT-M were not detected. In contrast, C2GnT-M transcripts were detected in A549 lung carcinoma cell line where C2GnT-L transcripts were not detected (FIG. 8, far right). These results indicate that C2GnT-M and C2GnT-L are differentially expressed in different tissues.

Previous reports have indicated that C4GnT activity is associated with the presence of C2GnT activity when various mucin-producing tissues are examined (Brockhausen et al., *Eur. J. Biochem.* 157:463–474 (1986); Ropp et al., *J. Biol. Chem.* 266:23863–23871 (1991); Yang et al., *Glycobiology* 4:873–884 (1994); Vavasseur et al. *Glycobiology* 5:351–357 (1995), each of which is herein incorporated by reference). It is likely that C2GnT-M is responsible for C4GnT activity in these tissues. In small intestine, colon and stomach, significant amounts of the transcripts for C2GnT-L and C2GnT-M were detected, suggesting that both enzymes contribute to the C2GnT activity in these tissues.

EXAMPLE V

Isolation of Mouse C2GnT-M

This example shows the isolation of nucleic acid molecules encoding mouse C2GnT-M.

In order to isolate mouse C2GnT-M, two sets of PCR primers, each corresponding to different regions of human C2GnT-M cDNA, were used to amplify homologous sequences present in a mouse genomic DNA library. The first set of primers, consisting of the CCL1 sense (SEQ ID NO: 6) and CCL2AS antisense (SEQ ID NO: 5) oligonucleotides, was designed to amplify nucleic acid sequences encoding at least a part of the "A" region, indicated in FIG. 5, that is highly conserved among β-1-6-N-acetylglucosaminyltransferases. Amplification with the CCL1 and CCL2AS primers resulted in the isolation of a 192 nucleotide mouse C2GnT-M nucleic acid molecule, designated CCL1, having the nucleotide sequence shown in FIG. 9A (SEQ ID NO: 9). The CCL1 fragment of mouse C2GnT-M is 79.7% identical to the corresponding fragment of the nucleic acid molecule encoding human C2GnT-M (fragment of SEQ ID NO: 1). The alignment of CCL1 with human C2GnT-M is shown in FIG. 9A. The amino acid sequence encoded by CCL1 is shown in FIG. 9B (SEQ ID NO: 10). The 64 amino acid CCL1 polypeptide is 79.7% identical to the corresponding fragment of human C2GnT-M (fragment of SEQ ID NO: 2), as shown in FIG. 9B.

The second set of primers consisted of the HCC-IS3 sense primer, which has the sequence 5'-TGCTCTAGAGCAGAGATGGTCCAGGCTCTCAAG-3' (SEQ ID NO: 11), and the HCC-IS4AS antisense primer, which has the sequence 5'-CGGGGTACCCGGGAAGCCACAATGTACGCATTCC-3' (SEQ ID NO: 12). This set of primers was designed to amplify nucleic acid sequences encoding at least a part of the amino acid sequence between the "A" and "B" regions indicated in FIG. 5. Amplification of mouse genomic DNA with the HCC-IS3 and HCC-IS4AS primers resulted in the isolation of a 148 nucleotide mouse C2GnT-M nucleic acid molecule, designated IS3, having the nucleotide sequence shown in FIG. 10A (SEQ ID NO: 13). The IS3 fragment of mouse C2GnT-M is 77.7% identical to the corresponding fragment of the nucleic acid molecule encoding human C2GnT-M (fragment of SEQ ID NO: 1). The alignment of IS3 with human C2GnT-M is shown in FIG. 10A. The amino acid sequence encoded by IS3 is shown in FIG. 10B (SEQ ID NO: 14). The 50 amino acid CCL1 polypeptide is 72.0% identical to the corresponding fragment of human C2GnT-M (fragment of SEQ ID NO: 2), as shown in FIG. 10B.

Isolation of full-length mouse C2GnT-M cDNA is accomplished using 5' and 3' RACE as described above in Example I.

Throughout this application various publications have been referenced within parentheses. The disclosure of these publications in their entireties are hereby incorporated by reference in this application in order to more fully describe the state of the art to which this invention applies.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

We claim:

1. A substantially pure C2GnT-M polypeptide wherein the C2GnT-M polypeptide comprises the amino acid sequence of SEQ ID NO: 2 or a fragment thereof, wherein said C2GnT-M polypeptide or fragment thereof has core 2, core 4 and I branching β-1-6-N-acetylglucosylaminyltransferase activities.

2. The C2GnT-M polypeptide of claim 1, comprising the amino acid sequence designated SEQ ID NO: 2.

3. The C2GnT-M polypeptide of claim 1, consisting of the amino acid sequence designated SEQ ID NO: 2.

4. The C2GnT-M polypeptide of claim 1, comprising the amino acid residues 34–438 of the amino acid sequence designated SEQ ID NO: 2.

5. The C2GnT-M polypeptide of claim 1, consisting of amino acid residues 34–438 of SEQ ID NO: 2.

6. The C2GnT-M polypeptide of claim 1, comprising amino acid residues 123–244 of the amino acid sequence designated SEQ ID NO: 2.

7. The C2GnT-M polypeptide of claim 1, comprising amino acid residues 323–348 of the amino acid sequence designated SEQ ID NO: 2.

8. The C2GnT-M polypeptide of claim 1, comprising amino acid residues 390–413 of the amino acid sequence designated SEQ ID NO: 2.

9. A substantially pure C2GnT-M polypeptide or fragment thereof which is encoded by a nucleic acid which has at least 70% homology to SEQ ID NO: 1, wherein said C2GnT-M polypeptide or fragment thereof has core 2, core 4 and I branching 3-1-6-N-acetylglucosylaminyltransferase activities.

10. The substantially pure C2GnT-M polypeptide or fragment thereof of claim 9 which is encoded by a nucleic acid which has at least 80% homology to SEQ ID NO: 1.

11. The substantially pure C2GnT-M polypeptide or fragment thereof of claim 10 which is encoded by a nucleic acid which has at least 90% homology to SEQ ID NO: 1.

12. A substantially pure C2GnT-M peptide consisting of amino acid residues 123–244 of the amino acid sequence designated SEQ ID NO: 2 wherein said peptide is immunogenic.

13. A substantially pure C2GnT-M peptide consisting of amino acid residues 323–348 of the amino acid sequence designated SEQ ID NO: 2 wherein said peptide is immunogenic.

14. A substantially pure C2GnT-M peptide consisting of amino acid residues 390–413 of the amino acid sequence designated SEQ ID NO: 2 wherein said peptide is immunogenic.

15. A substantially pure naturally occurring mouse C2GnT-M polypeptide having core 2, core 4 and I branching $\beta$-1-6-N-acetylglucosylaminyltransferase activities, wherein said polypeptide comprises SEQ ID NO: 14.

16. The C2GnT-M polypeptide of claim 15, that further comprises SEQ ID NO: 10.

17. A method of modifying an acceptor molecule, comprising contacting said acceptor molecule with the polypeptide of any of claims 1, 3, 4, 2, 6, 7, 8, 9, 10, 11, 15 and 16 under conditions that allow addition of core 2, core 4 or I GlcNAc linkages to said acceptor molecule.

* * * * *

SEQUENCE LISTING

```
<160> NUMBER OF SEQ ID NOS: 14

<210> SEQ ID NO 1
<211> LENGTH: 2128
<212> TYPE: DNA
<213> ORGANISM: Homo sapiens
<220> FEATURE:
<221> NAME/KEY: CDS
<222> LOCATION: (354)..(1670)

<400> SEQUENCE: 1
cttgagaatg tttctgcatg atttctctgg gcttgctgtc ttacctgaga gcaggaagtc      60
aaaaggagag tgatggagcc acctgctgcc ctctactttg cagatattaa agaggagcct     120
gaaactgttc cttggacatc ttatgaatgt cagaaaatac cttttggagg gttagaagat     180 cagggacat ggttgttcac atttgctgcc acggaacacc gccagtcttc acttggaaac      240
agaatcacgc cttgtgaaga gatcatccct aagcaggaga gaagctacta aaggattgtg     300
tcctcctcca ccttccctgt gctcggtctc cacctgtctc ccattctgtg acg atg        356
                                                            Met
                                                              1 gtt caa tgg aag aga ctc tgc cag ctg cat tac ttg tgg gct ctg ggc       404
Val Gln Trp Lys Arg Leu Cys Gln Leu His Tyr Leu Trp Ala Leu Gly
            5                  10                  15 tgc tat atg ctg ctg gcc act gtg gct ctg aaa ctt tct ttc agg ttg       452
Cys Tyr Met Leu Leu Ala Thr Val Ala Leu Lys Leu Ser Phe Arg Leu
        20                  25                  30
```

-continued

```
aag tgt gac tct gac cac ttg ggt ctg gag tcc agg gaa tct caa agc      500
Lys Cys Asp Ser Asp His Leu Gly Leu Glu Ser Arg Glu Ser Gln Ser
     35                  40                  45 cag tac tgt agg aat atc ttg tat aat ttc ctg aaa ctt cca gca aag      548
Gln Tyr Cys Arg Asn Ile Leu Tyr Asn Phe Leu Lys Leu Pro Ala Lys
 50                  55                  60                  65 agg tct atc aac tgt tca ggg gtc acc cga ggg gac caa gag gca gtg      596
Arg Ser Ile Asn Cys Ser Gly Val Thr Arg Gly Asp Gln Glu Ala Val
                 70                  75                  80 ctt cag gct att ctg aat aac ctg gag gtc aag aag aag cga gag cct      644
Leu Gln Ala Ile Leu Asn Asn Leu Glu Val Lys Lys Lys Arg Glu Pro
             85                  90                  95 ttc aca gac acc cac tac ctc tcc ctc acc aga gac tgt gag cac ttc      692
Phe Thr Asp Thr His Tyr Leu Ser Leu Thr Arg Asp Cys Glu His Phe
            100                 105                 110 aag gct gaa agg aag ttc ata cag ttc cca ctg agc aaa gaa gag gtg      740
Lys Ala Glu Arg Lys Phe Ile Gln Phe Pro Leu Ser Lys Glu Glu Val
        115                 120                 125 gag ttc cct att gca tac tct atg gtg att cat gag aag att gaa aac      788
Glu Phe Pro Ile Ala Tyr Ser Met Val Ile His Glu Lys Ile Glu Asn
130                 135                 140                 145 ttt gaa agg cta ctg cga gct gtg tat gcc cct cag aac ata tac tgt      836
Phe Glu Arg Leu Leu Arg Ala Val Tyr Ala Pro Gln Asn Ile Tyr Cys
                150                 155                 160 gtc cat gtg gat gag aag tcc cca gaa act ttc aaa gag gcg gtc aaa      884
Val His Val Asp Glu Lys Ser Pro Glu Thr Phe Lys Glu Ala Val Lys
            165                 170                 175 gca att att tct tgc ttc cca aat gtc ttc ata gcc agt aag ctg gtt      932
Ala Ile Ile Ser Cys Phe Pro Asn Val Phe Ile Ala Ser Lys Leu Val
        180                 185                 190 cgg gtg gtt tat gcc tcc tgg tcc agg gtg caa gct gac ctc aac tgc      980
Arg Val Val Tyr Ala Ser Trp Ser Arg Val Gln Ala Asp Leu Asn Cys
195                 200                 205 atg gaa gac ttg ctc cag agc tca gtg ccg tgg aaa tac ttc ctg aat     1028
Met Glu Asp Leu Leu Gln Ser Ser Val Pro Trp Lys Tyr Phe Leu Asn
210                 215                 220                 225 aca tgt ggg acg gac ttt cct ata aag agc aat gca gag atg gtc cag     1076
Thr Cys Gly Thr Asp Phe Pro Ile Lys Ser Asn Ala Glu Met Val Gln
                230                 235                 240 gct ctc aag atg ttg aat ggg agg aat agc atg gag tca gag gta cct     1124
Ala Leu Lys Met Leu Asn Gly Arg Asn Ser Met Glu Ser Glu Val Pro
            245                 250                 255 cct aag cac aaa gaa acc cgc tgg aaa tat cac ttt gag gta gtg aga     1172
Pro Lys His Lys Glu Thr Arg Trp Lys Tyr His Phe Glu Val Val Arg
        260                 265                 270 gac aca tta cac cta acc aac aag aag aag gat cct ccc cct tat aat     1220
Asp Thr Leu His Leu Thr Asn Lys Lys Lys Asp Pro Pro Pro Tyr Asn
275                 280                 285 tta act atg ttt aca ggg aat gcg tac att gtg gct tcc cga gat ttc     1268
Leu Thr Met Phe Thr Gly Asn Ala Tyr Ile Val Ala Ser Arg Asp Phe
290                 295                 300                 305 gtc caa cat gtt ttg aag aac cct aaa tcc caa caa ctg att gaa tgg     1316
Val Gln His Val Leu Lys Asn Pro Lys Ser Gln Gln Leu Ile Glu Trp
                310                 315                 320 gta aaa gac act tat agc cca gat gaa cac ctc tgg gcc acc ctt cag     1364
Val Lys Asp Thr Tyr Ser Pro Asp Glu His Leu Trp Ala Thr Leu Gln
            325                 330                 335 cgt gca cgg tgg atg cct ggc tct gtt ccc aac cac ccc aag tac gac     1412
Arg Ala Arg Trp Met Pro Gly Ser Val Pro Asn His Pro Lys Tyr Asp
        340                 345                 350
```

-continued

```
atc tca gac atg act tct att gcc agg ctg gtc aag tgg cag ggt cat       1460
Ile Ser Asp Met Thr Ser Ile Ala Arg Leu Val Lys Trp Gln Gly His
    355                 360                 365 gag gga gac atc gat aag ggt gct cct tat gct ccc tgc tct gga atc       1508
Glu Gly Asp Ile Asp Lys Gly Ala Pro Tyr Ala Pro Cys Ser Gly Ile
370                 375                 380                 385 cac cag cgg gct atc tgc gtt tat ggg gct ggg gac ttg aat tgg atg       1556
His Gln Arg Ala Ile Cys Val Tyr Gly Ala Gly Asp Leu Asn Trp Met
                390                 395                 400 ctt caa aac cat cac ctg ttg gcc aac aag ttt gac cca aag gta gat       1604
Leu Gln Asn His His Leu Leu Ala Asn Lys Phe Asp Pro Lys Val Asp
            405                 410                 415 gat aat gct ctt cag tgc tta gaa gaa tac cta cgt tat aag gcc atc       1652
Asp Asn Ala Leu Gln Cys Leu Glu Glu Tyr Leu Arg Tyr Lys Ala Ile
        420                 425                 430 tat ggg act gaa ctt tga gacacactat gagagcgttg ctacctgtgg              1700
Tyr Gly Thr Glu Leu
        435 ggcaagagca tgtacaaaca tgctcagaac ttgctgggac agtgtgggtg ggagaccagg     1760 gctttgcaat tcgtggcatc ctttaggata agagggctgc tattagattg tgggtaagta     1820 gatcttttgc cttgcaaatt gctgcctggg tgaatgctgc ttgttctctc accctaacc      1880 ctagtagttc ctccactaac tttctcacta agtgagaatg agaactgctg tgatagggag     1940 agtgaaggag ggatatgtgg tagagcactt gatttcagtt gaatgcctgc tggtagcttt     2000 tccattctgt ggagctgccg ttcctaataa ttccaggttt ggtaacgtgg aggagaactt     2060 tgatggaaag agaacttcct tctgtactgt taacttaaaa ataaatactc ctgatcaaaa     2120 aaaaaaaa                                                              2128

<210> SEQ ID NO 2
<211> LENGTH: 438
<212> TYPE: PRT
<213> ORGANISM: Homo sapiens

<400> SEQUENCE: 2

Met Val Gln Trp Lys Arg Leu Cys Gln Leu His Tyr Leu Trp Ala Leu
1               5                   10                  15

Gly Cys Tyr Met Leu Leu Ala Thr Val Ala Leu Lys Leu Ser Phe Arg
            20                  25                  30

Leu Lys Cys Asp Ser Asp His Leu Gly Leu Glu Ser Arg Glu Ser Gln
        35                  40                  45

Ser Gln Tyr Cys Arg Asn Ile Leu Tyr Asn Phe Leu Lys Leu Pro Ala
    50                  55                  60

Lys Arg Ser Ile Asn Cys Ser Gly Val Thr Arg Gly Asp Gln Glu Ala
65                  70                  75                  80

Val Leu Gln Ala Ile Leu Asn Asn Leu Glu Val Lys Lys Arg Glu
                85                  90                  95

Pro Phe Thr Asp Thr His Tyr Leu Ser Leu Thr Arg Asp Cys Glu His
                100                 105                 110

Phe Lys Ala Glu Arg Lys Phe Ile Gln Phe Pro Leu Ser Lys Glu Glu
            115                 120                 125

Val Glu Phe Pro Ile Ala Tyr Ser Met Val Ile His Glu Lys Ile Glu
        130                 135                 140

Asn Phe Glu Arg Leu Leu Arg Ala Val Tyr Ala Pro Gln Asn Ile Tyr
145                 150                 155                 160
```

-continued

```
Cys Val His Val Asp Glu Lys Ser Pro Glu Thr Phe Lys Glu Ala Val
                165                 170                 175
Lys Ala Ile Ile Ser Cys Phe Pro Asn Val Phe Ile Ala Ser Lys Leu
            180                 185                 190
Val Arg Val Val Tyr Ala Ser Trp Ser Arg Val Gln Ala Asp Leu Asn
        195                 200                 205
Cys Met Glu Asp Leu Leu Gln Ser Ser Val Pro Trp Lys Tyr Phe Leu
    210                 215                 220
Asn Thr Cys Gly Thr Asp Phe Pro Ile Lys Ser Asn Ala Glu Met Val
225                 230                 235                 240
Gln Ala Leu Lys Met Leu Asn Gly Arg Asn Ser Met Glu Ser Glu Val
                245                 250                 255
Pro Pro Lys His Lys Glu Thr Arg Trp Lys Tyr His Phe Glu Val Val
            260                 265                 270
Arg Asp Thr Leu His Leu Thr Asn Lys Lys Asp Pro Pro Tyr
        275                 280                 285
Asn Leu Thr Met Phe Thr Gly Asn Ala Tyr Ile Val Ala Ser Arg Asp
    290                 295                 300
Phe Val Gln His Val Leu Lys Asn Pro Lys Ser Gln Gln Leu Ile Glu
305                 310                 315                 320
Trp Val Lys Asp Thr Tyr Ser Pro Asp Glu His Leu Trp Ala Thr Leu
                325                 330                 335
Gln Arg Ala Arg Trp Met Pro Gly Ser Val Pro Asn His Pro Lys Tyr
            340                 345                 350
Asp Ile Ser Asp Met Thr Ser Ile Ala Arg Leu Val Lys Trp Gln Gly
        355                 360                 365
His Glu Gly Asp Ile Asp Lys Gly Ala Pro Tyr Ala Pro Cys Ser Gly
    370                 375                 380
Ile His Gln Arg Ala Ile Cys Val Tyr Gly Ala Gly Asp Leu Asn Trp
385                 390                 395                 400
Met Leu Gln Asn His His Leu Leu Ala Asn Lys Phe Asp Pro Lys Val
                405                 410                 415
Asp Asp Asn Ala Leu Gln Cys Leu Glu Glu Tyr Leu Arg Tyr Lys Ala
            420                 425                 430
Ile Tyr Gly Thr Glu Leu
        435

<210> SEQ ID NO 3
<211> LENGTH: 428
<212> TYPE: PRT
<213> ORGANISM: Homo sapiens

<400> SEQUENCE: 3

Met Leu Arg Thr Leu Leu Arg Arg Arg Leu Phe Ser Tyr Pro Thr Lys
1               5                   10                  15
Tyr Tyr Phe Met Val Leu Val Leu Ser Leu Ile Thr Phe Ser Val Leu
                20                  25                  30
Arg Ile His Gln Lys Pro Glu Phe Val Ser Val Arg His Leu Glu Leu
            35                  40                  45
Ala Gly Glu Asn Pro Ser Ser Asp Ile Asn Cys Thr Lys Val Leu Gln
        50                  55                  60
Gly Asp Val Asn Glu Ile Gln Lys Val Lys Leu Glu Ile Leu Thr Val
65                  70                  75                  80
```

```
Lys Phe Lys Lys Arg Pro Arg Trp Thr Pro Asp Asp Tyr Ile Asn Met
                85                  90                  95

Thr Ser Asp Cys Ser Ser Phe Ile Lys Arg Arg Lys Tyr Ile Val Glu
            100                 105                 110

Pro Leu Ser Lys Glu Glu Ala Glu Phe Pro Ile Ala Tyr Ser Ile Val
        115                 120                 125

Val His His Lys Ile Glu Met Leu Asp Arg Leu Leu Arg Ala Ile Tyr
    130                 135                 140

Met Pro Gln Asn Phe Tyr Cys Val His Val Asp Thr Lys Ser Glu Asp
145                 150                 155                 160

Ser Tyr Leu Ala Ala Val Met Gly Ile Ala Ser Cys Phe Ser Asn Val
            165                 170                 175

Phe Val Ala Ser Arg Leu Glu Ser Val Val Tyr Ala Ser Trp Ser Arg
            180                 185                 190

Val Gln Ala Asp Leu Asn Cys Met Lys Asp Leu Tyr Ala Met Ser Ala
        195                 200                 205

Asn Trp Lys Tyr Leu Ile Asn Leu Cys Gly Met Asp Phe Pro Ile Lys
    210                 215                 220

Thr Asn Leu Glu Ile Val Arg Lys Leu Lys Leu Leu Met Gly Glu Asn
225                 230                 235                 240

Asn Leu Glu Thr Glu Arg Met Pro Ser His Lys Glu Glu Arg Trp Lys
            245                 250                 255

Lys Arg Tyr Glu Val Val Asn Gly Lys Leu Thr Asn Thr Gly Thr Val
            260                 265                 270

Lys Met Leu Pro Pro Leu Glu Thr Pro Leu Phe Ser Gly Ser Ala Tyr
        275                 280                 285

Phe Val Val Ser Arg Glu Tyr Val Gly Tyr Val Leu Gln Asn Glu Lys
    290                 295                 300

Ile Gln Lys Leu Met Glu Trp Ala Gln Asp Thr Tyr Ser Pro Asp Glu
305                 310                 315                 320

Tyr Leu Trp Ala Thr Ile Gln Arg Ile Pro Glu Val Pro Gly Ser Leu
            325                 330                 335

Pro Ala Ser His Lys Tyr Asp Leu Ser Asp Met Gln Ala Val Ala Arg
            340                 345                 350

Phe Val Lys Trp Gln Tyr Phe Glu Gly Asp Val Ser Lys Gly Ala Pro
        355                 360                 365

Tyr Pro Pro Cys Asp Gly Val His Val Arg Ser Val Cys Ile Phe Gly
    370                 375                 380

Ala Gly Asp Leu Asn Trp Met Leu Arg Lys His His Leu Phe Ala Asn
385                 390                 395                 400

Lys Phe Asp Val Asp Val Asp Leu Phe Ala Ile Gln Cys Leu Asp Glu
            405                 410                 415

His Leu Arg His Lys Ala Leu Glu Thr Leu Lys His
            420                 425

<210> SEQ ID NO 4
<211> LENGTH: 400
<212> TYPE: PRT
<213> ORGANISM: Homo sapiens

<400> SEQUENCE: 4

Met Pro Leu Ser Met Arg Tyr Leu Phe Ile Ile Ser Val Ser Ser Val
 1               5                  10                  15

Ile Ile Phe Ile Val Phe Ser Val Phe Asn Phe Gly Gly Asp Pro Ser
            20                  25                  30
```

```
Phe Gln Arg Leu Asn Ile Ser Asp Pro Leu Arg Leu Thr Gln Val Cys
        35                  40                  45

Thr Ser Phe Ile Asn Gly Lys Thr Arg Phe Leu Trp Lys Asn Lys Leu
 50                  55                  60

Met Ile His Glu Lys Ser Ser Cys Lys Glu Tyr Leu Thr Gln Ser His
 65                  70                  75                  80

Tyr Ile Thr Ala Pro Leu Ser Lys Glu Glu Ala Asp Phe Pro Leu Ala
                 85                  90                  95

Tyr Ile Met Val Ile His His Phe Asp Thr Phe Ala Arg Leu Phe
            100                 105                 110

Arg Ala Ile Tyr Met Pro Gln Asn Ile Tyr Cys Val His Val Asp Glu
            115                 120                 125

Lys Ala Thr Glu Phe Lys Asp Ala Val Glu Gln Leu Leu Ser Cys
130                 135                 140

Phe Pro Asn Ala Phe Leu Ala Ser Lys Met Glu Pro Val Val Tyr Gly
145                 150                 155                 160

Gly Ile Ser Arg Leu Gln Ala Asp Leu Asn Cys Ile Arg Asp Leu Ser
                165                 170                 175

Ala Phe Glu Val Ser Trp Lys Tyr Val Ile Asn Thr Cys Gly Gln Asp
            180                 185                 190

Phe Pro Leu Lys Thr Asn Lys Glu Ile Val Gln Tyr Leu Lys Gly Phe
            195                 200                 205

Lys Gly Lys Asn Ile Thr Pro Gly Val Leu Pro Pro Ala His Ala Ile
210                 215                 220

Gly Arg Thr Lys Tyr Val His Gln Glu His Leu Gly Lys Glu Leu Ser
225                 230                 235                 240

Tyr Val Ile Arg Thr Thr Ala Leu Lys Pro Pro Pro His Asn Leu
                245                 250                 255

Thr Ile Tyr Phe Gly Ser Ala Tyr Val Ala Leu Ser Arg Glu Phe Ala
            260                 265                 270

Asn Phe Val Leu His Asp Pro Arg Ala Val Asp Leu Leu Gln Trp Ser
            275                 280                 285

Lys Asp Thr Phe Ser Pro Asp Glu His Phe Trp Val Thr Leu Asn Arg
290                 295                 300

Ile Pro Gly Val Pro Gly Ser Met Pro Asn Ala Ser Trp Thr Gly Asn
305                 310                 315                 320

Leu Arg Ala Ile Lys Trp Ser Asp Met Glu Asp Arg His Gly Gly Cys
                325                 330                 335

His Gly His Tyr Val His Gly Ile Cys Ile Tyr Gly Asn Gly Asp Leu
            340                 345                 350

Lys Trp Leu Val Asn Ser Pro Ser Leu Phe Ala Asn Lys Phe Glu Leu
            355                 360                 365

Asn Thr Tyr Pro Leu Thr Val Glu Cys Leu Glu Leu Arg His Arg Glu
            370                 375                 380

Arg Thr Leu Asn Gln Ser Glu Thr Ala Ile Gln Pro Ser Trp Tyr Phe
385                 390                 395                 400
```

<210> SEQ ID NO 5
<211> LENGTH: 28
<212> TYPE: DNA
<213> ORGANISM: Homo sapiens

<400> SEQUENCE: 5
ccagcttact ggctatgaag acatttgg                                    28

<210> SEQ ID NO 6
<211> LENGTH: 27
<212> TYPE: DNA
<213> ORGANISM: Homo sapiens

<400> SEQUENCE: 6
gagcacttca aggctgaaag gaagttc                                27

<210> SEQ ID NO 7
<211> LENGTH: 25
<212> TYPE: DNA
<213> ORGANISM: Homo sapiens

<400> SEQUENCE: 7 tcagggtca cccgagggga ccaag                                   25

<210> SEQ ID NO 8
<211> LENGTH: 24
<212> TYPE: DNA
<213> ORGANISM: Homo sapiens

<400> SEQUENCE: 8
ctccacctct tctttgctca gtgg                                   24

<210> SEQ ID NO 9
<211> LENGTH: 192
<212> TYPE: DNA
<213> ORGANISM: Mus musculus
<220> FEATURE:
<221> NAME/KEY: CDS
<222> LOCATION: (1)..(192)

<400> SEQUENCE: 9 ata cag gtc cca ctg agc aag gaa gag gcc agc ttc ccc att gcg tac      48
Ile Gln Val Pro Leu Ser Lys Glu Glu Ala Ser Phe Pro Ile Ala Tyr
 1               5                  10                  15 tcc atg gtg gtg cat gag aag att gag aac ttc gaa agg ttg ctg cga      96
Ser Met Val Val His Glu Lys Ile Glu Asn Phe Glu Arg Leu Leu Arg
             20                  25                  30 gct gtg tac acc cct cag aat gta tac tgt gtc cac atg gat cag aag     144
Ala Val Tyr Thr Pro Gln Asn Val Tyr Cys Val His Met Asp Gln Lys
         35                  40                  45 tct tca gaa ccc ttt aag cag gca gtc ggg gcc atc gtg tca tgc ttc     192
Ser Ser Glu Pro Phe Lys Gln Ala Val Gly Ala Ile Val Ser Cys Phe
     50                  55                  60

SEQ ID NO 10

<211> LENGTH: 64
<212> TYPE: PRT
<213> ORGANISM: Mus musculus

<400> SEQUENCE: 10

Ile Gln Val Pro Leu Ser Lys Glu Glu Ala Ser Phe Pro Ile Ala Tyr
 1               5                  10                  15

Ser Met Val Val His Glu Lys Ile Glu Asn Phe Glu Arg Leu Leu Arg
             20                  25                  30

Ala Val Tyr Thr Pro Gln Asn Val Tyr Cys Val His Met Asp Gln Lys
         35                  40                  45

Ser Ser Glu Pro Phe Lys Gln Ala Val Gly Ala Ile Val Ser Cys Phe
     50                  55                  60

```
<210> SEQ ID NO 11
<211> LENGTH: 33
<212> TYPE: DNA
<213> ORGANISM: Homo sapiens

<400> SEQUENCE: 11
tgctctagag cagagatggt ccaggctctc aag                              33

<210> SEQ ID NO 12
<211> LENGTH: 34
<212> TYPE: DNA
<213> ORGANISM: Homo sapiens

<400> SEQUENCE: 12
cggggtaccc gggaagccac aatgtacgca ttcc                             34

<210> SEQ ID NO 13
<211> LENGTH: 147
<212> TYPE: DNA
<213> ORGANISM: Mus musculus
<220> FEATURE:
<221> NAME/KEY: CDS
<222> LOCATION: (1)..(147)

<400> SEQUENCE: 13 cta ttg aaa ggg cag aac agt atg gag tca gag gta cca cct cca cat    48
Leu Leu Lys Gly Gln Asn Ser Met Glu Ser Glu Val Pro Pro Pro His
 1               5                  10                  15 aaa aaa tcc cgc tgg aaa tat cac tat gag gtg aca gac aca ttg cac    96
Lys Lys Ser Arg Trp Lys Tyr His Tyr Glu Val Thr Asp Thr Leu His
             20                  25                  30 atg acc agc aag agg aag acg ccg cca cct aat aac cta acc atg ttc   144
Met Thr Ser Lys Arg Lys Thr Pro Pro Pro Asn Asn Leu Thr Met Phe
         35                  40                  45 act                                                                147
Thr

<210> SEQ ID NO 14
<211> LENGTH: 49
<212> TYPE: PRT
<213> ORGANISM: Mus musculus

<400> SEQUENCE: 14

Leu Leu Lys Gly Gln Asn Ser Met Glu Ser Glu Val Pro Pro His
 1               5                  10                  15

Lys Lys Ser Arg Trp Lys Tyr His Tyr Glu Val Thr Asp Thr Leu His
             20                  25                  30

Met Thr Ser Lys Arg Lys Thr Pro Pro Pro Asn Asn Leu Thr Met Phe
         35                  40                  45

Thr
```